United States Patent [19]

Puhler et al.

[11] Patent Number: 4,782,022

[45] Date of Patent: Nov. 1, 1988

[54] NITROGEN FIXATION REGULATOR GENES

[75] Inventors: Alfred Puhler; Helmut Reilaender, both of Bielefeld; Gerhard Weber, Werther, all of Fed. Rep. of Germany

[73] Assignee: Lubrizol Genetics, Inc., Wickliffe, Ohio

[21] Appl. No.: 737,029

[22] Filed: May 22, 1985

Related U.S. Application Data

[63] Continuation-in-part of Ser. No. 616,586, Jun. 4, 1984, abandoned.

[51] Int. Cl.⁴ .................. C12N 15/00; C12N 1/20; C07H 15/12
[52] U.S. Cl. .................. 435/172.3; 435/253; 435/320; 935/29; 935/56; 935/72; 536/27
[58] Field of Search ............ 435/172.3, 253, 320; 935/27, 30, 35, 61, 62, 64, 67; 536/27

[56] References Cited

U.S. PATENT DOCUMENTS 4,448,885  5/1984  Schnepf et al. .................. 935/11

OTHER PUBLICATIONS

Barton & Brill (1983) "Prospects in Genetic Engineering" Science 219:671-76.
Ow & Ausubel (1983) "Regulation of Nitrogen . . ." Nature 301:307-13.
Zimmerman et al. (1983) "A Region which Regulates . . ." in Plant Molecular Biol. (Goldberg, Ed.) pp. 237-42.
Simon et al. (1983) "Victor Plasmids for . . ." Proc. of Bielefield Symp., Springer-Verlag, W. Germany pp. 98-106.
Fuhrmann et al. (1982) "Coding Properties of Cloned . . ." Mol Gen Gevet 187:419-25.
Selvaraj et al. (1983) "Suicide Plasmid Vehicles . . ." J of Bacteriol 156(3):1292-1300.
Corbin et al. (1983) "Organization & Expression . . ." PNAS 80:3005-9.
Kennedy et al. (1983) Nature 301:626-628.
Szeto et al. (1984) Cell 36(4):1035-1044.
Vincent, J. M. (1980) In: *Symbiotic Associations and Cyanobacteria, Nitrogen Fixation* vol. 2 (W. E. Newton and W. H. Orne-Johnson, eds.), Baltimore, University Park Press, pp. 103-129.
Verma, D. P. S. et al. (1981) In: *Current Perspective in Nitrogen Fixation* (A. H. Gibson & W. E. Newton, eds.) Canberra, Australia Acad. of Science, pp. 205-208.
Scott, D. B. et al. (1976) Nature 263:703-705.
Ruvkun, G. B. et al. (1982) Cell 29:551-559.
Schetgens, T. M. P. et al., (1984) In: *Advances in Nitrogen Fixation Research* (C. Veeger & W. E. Newton, eds.), Marinus Nijhoff/Dr. W. Junk Publishers, the Hague p. 699.
Scott, K. F. et al. (1983) DNA 2:141-148.
Trinick, M. J. (1980) J. Appl. Bacteriol. 49:39-53.
Ruvkun, G. B. and F. M. Ausubel (1980) Proc. Natl. Acad. Sci. U.S.A. 77:191-195.
Scott, K. F. et al. (1981) J. Mol. Appl. Genet. 1:71-81.
Eady, R. R. & B. E. Smith (1979) In: *A Treatise on Dinitrogen Fixation I, II* (Hardy, R. W. et al., eds.), Wiley Press, New York, pp. 399-490.
Ruvkun, G. B. and F. M. Ausubel (1981) Nature 289:85-88.
Ruvkun, G. B. et al. (1980) Cold Spring Harbor Symp. Quant. Biol. 45:492-497.
Weber, G. and A. Puhler (1982) Plant Mol. Biol. 1:305-320.
Puhler, A. et al. (1983) In: Advances in Nitrogen Fixation Research (C. Veeger and W. E. Newton, eds.), Martinus Nijhoff/Dr. Junk Publishers, The Hague. p. 609.
Sundarsan, V. et al. (1983) Nature 301:728-732.
Sundaresan, V. et al. (1983) Proc. Natl. Acad. Sci. U.S.A. 80:4030-4034.

*Primary Examiner*—Charles F. Warren
*Assistant Examiner*—David T. Fox
*Attorney, Agent, or Firm*—Greenlee and Associates

[57] ABSTRACT

Isolation and characterization of a gene which activated nitrogen fixation genes of *Rhizobium meliloti* when that bacterium is in a symbiotic relationship with a plant is disclosed. This newly discovered gene, designated fix D, can activate the nifHD promoter. A method of making this inducible gene constitutive is presented. This is useful for making nifHD constitutive. The combination of the fixD promoter with heterologous structural genes is taught. Such combinations are useful for limiting expression of an encoded protein to rhizobia involved in a symbiotic relationship with a plant. Plasmids and methods useful in performance of this invention are also disclosed.

25 Claims, 15 Drawing Sheets

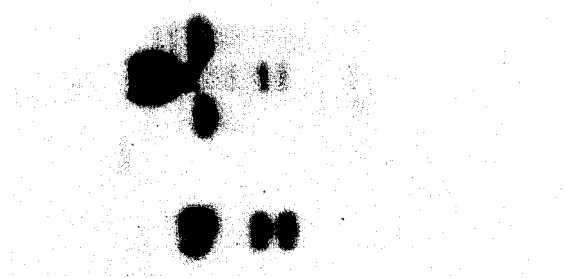
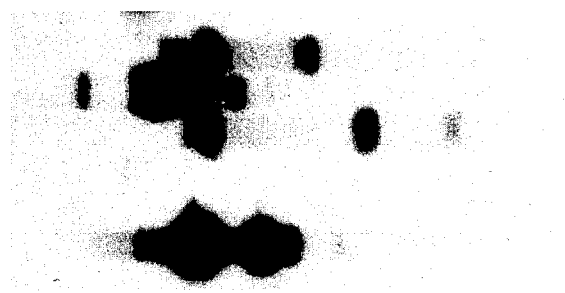
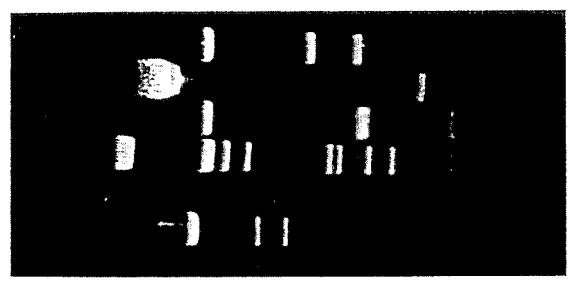

FIG. 5-1

```
            H               H                               S
         NIMH            I HHT                              AH
         LNSH            N HAT                              UA
         APTA            P AEH                              9E
         3111            1 122                              63
    CTTCACAAAGAGACATGCGCAAACAGGACAAGCGCTCCGCCGAAATTTACAGCATATCAAAGGCTCTGATGGCCCCCACTCGTCTTGAGACCACGCTTAA
401 ----------+---------+---------+---------+---------+---------+---------+---------+---------+---------+ 500
    GAAGTGTTTCTCTGTACGCGTTTGTCCTGTTCGCGAGGCGGCTTTAAATGTCGTATAGTTTCCGAGACTACCGGGGGTGAGCAGAACTCTGGTGCGAATT

S  Q  R  D  M  R  K  Q  D  K  R  S  A  E  I  Y  S  I  S  K  A  L  M  A  P  T  R  L  E  T  T  L  N

H     H    H F  FF    H        H         H                                  F
                        IM    IMH  NISHN NNS  I ATHX I H AG                                         N
                        NN    NSH  LNPHU UUS  N VAGH N P HI                                         U
                        FL    PTA  APHA4 D4T  F AQAO F A AD                                         4
                        11    111  3111H 2H2  1 1111 1 2 21                                         H
                        /      /     /   /    /      /   /
    CAATTTCGTGAATACCCTCTCTTTGATTCTGCGCATGCGCCGCGGCGGACTCGAGATTCCGGCGTCGGAAGGAGAGACAAAGATAACAGCGGCTACCCGC
501 ----------+---------+---------+---------+---------+---------+---------+---------+---------+---------+ 600
    GTTAAAGCACTTATGGGAGAGAAACTAAGACGCGTACGCGGCGCCGCCTGAGCTCTAAGGCCGCAGCCTTCCTCTCTGTTTCTATTGTCGCCGATGGGCG

N  F  V  N  T  L  S  L  I  L  R  M  R  R  G  G  L  E  I  P  A  S  E  G  E  T  K  I  T  A  A  T  R

F                F                              S F
            N                HN          T        N         HNC N           R
            U           R    AU          T        L         PCR U           S
            4           S    E4          H        A         AIF 4           A
            H           A    3H          1        3         211 H           1
                        1                                      /
    AACAGCGGGTCTCCTTCTGCCGCTGATTATACTGTACCAAAGGCCGCAATAGACCAAGTCATGACTGCCGGGCGGCTGGTCGTACCAGACGTTTGCAACT
601 ----------+---------+---------+---------+---------+---------+---------+---------+---------+---------+ 700
    TTGTCGCCCAGAGGAAGACGGCGACTAATATGACATGGTTTCCGGCGTTATCTGGTTCAGTACTGACGGCCCGCCGACCAGCATGGTCTGCAAACGTTGA

N  S  G  S  P  S  A  A  D  Y  T  V  P  K  A  A  I  D  Q  V  M  T  A  G  R  L  V  V  P  D  V  C  N  S

S           H F    S              F F             S
         D  A    A           I NH   AA    B        NM N            TA
         D  L    U           N UH   VU    B        UN U            AU
         E  U    3           P DA   A9    V        4L 4            Q3
         1  1    A           1 21   26    1        H1 H            1A
                                           /      /
    CTGAGCTGTTCAAGGATCAGATAAAATGGCGCGGAATTGGTCCGACTGCCTTCATCGCTGCGGCGGTGGAGGTCGATCACGAAACGGGCGGAATGCTGTG
701 ----------+---------+---------+---------+---------+---------+---------+---------+---------+---------+ 800
    GACTCGACAAGTTCCTAGTCTATTTTACCGCGCCTTAACCAGGCTGACGGAAGTAGCGACGCCGCCACCTCCAGCTAGTGCTTTGCCCGCCTTACGACAC

E  L  F  K  D  Q  I  K  W  R  G  I  G  P  T  A  F  I  A  A  A  V  E  V  D  H  E  T  G  G  M  L  W

H   H                                      F              S
         T      I H I         MM   M M         R            HN     M       A H
         A      N H N         NB   N N         S            AU     N       U A
         Q      P A F         LO   L L         A            E4     L       9 E
         1      1 1 1         12   1 1         1            3H     1       6 3
    GTTCGAGTGCGCCAAGAGTCCGATTATGATTATGAGGAGGAGGTACACTTTCTTTCTATGGCCGCCAATCTTGCGGGGAGGGCCATTCGGCTTCATCGC
801 ----------+---------+---------+---------+---------+---------+---------+---------+---------+---------+ 900
    CAAGCTCACGCGGCTTCTCAGGCTAATACTAATACTCCTCCTCCATGTGAAAGAAAGATACCGGCGGTTAGAACGCCCCTCCCGGTAAGCCGAAGTAGCG

F  E  C  A  E  E  S  D  Y  D  Y  E  E  E  V  H  F  L  S  M  A  A  N  L  A  G  R  A  I  R  L  H  R

F             E
                               N      M   B  C                      B              F F
                               U      B   B  O                      B              N N
                               4      O   V  R                      V              U U
                               H      2   1  1                      1              4 4
                                                                                    H H
    ACAATCAGCAGGCGTGAGCGGACATTTGCCGAAGAGCAGCAAGAACAACAGAATTCACGTGATGAGCAGAGCCAGAGTTCCGCCCGCCAGCGGCTGCTCA
901 ----------+---------+---------+---------+---------+---------+---------+---------+---------+---------+ 1000
    TGTTAGTCGTCCGCACTCGCCTGTAAACGGCTTCTCGTCGTTCTTGTTGTCTTAAGTGCACTACTCGTCTCGGTCTCAAGGCGGGCGGTCGCCGACGAGT

T  I  S  R  R  E  R  T  F  A  E  E  Q  Q  E  Q  Q  N  S  R  D  E  Q  S  Q  S  S  A  R  Q  R  L  L  K

S                                                    B
              A                R            N    M                  S N                          DM
              U                S            L    N                  T L                          DS
              3                A            A    L                  X A                          ET
              A                1            3    1                  1 3                          12
                                                                                                  /
    AGAATGACGGGATCATCGGGGAAAGTACCGCCCTCATGACGGCGGTAGATACCGCCAAAGTCATGGCAGAGACCAATTCAATCGTTCTCCTTAGGGGAGA
1001 ---------+---------+---------+---------+---------+---------+---------+---------+---------+---------+ 1100
    TCTTACTGCCCTAGTAGCCCCTTTCATGGCGGGAGTACTGCCGCCATCTATGGCGGTTTCAGTACCGTCTCTGGTTAAGTTAGCAAGAGGAATCCCCTCT
```

FIG. 5-2

```
      N  D  G  I  I  G  E  S  T  A  L  M  T  A  V  D  T  A  K  V  M  A  E  T  N  S  I  V  L  L  R  G  E
                                        H                                            F H
                          A             T I                                          N I H      D
                          L             A N                                          U N H      D
                          U             Q F                                          D P A      E
                          1             1 1                                          2 1 1      1
                                                                                       /
     AACAGGAACTGGCAAGGAATGCTTTGCGAAGCTAATCCACCAGCATTCGACTCGGCAAAAAAAGCCCTTCATCAAGTTCAATTGCCCCGCGCTGTCTGAG
1101 ----------+---------+---------+---------+---------+---------+---------+---------+---------+---------+ 1200
     TTGTCCTTGACCGTTCCTTACGAAACGCTTCGATTAGGTGGTCGTAAGCTGAGCCGTTTTTTTCGGGAAGTAGTTCAAGTTAACGGGGCGCGACAGACTC

T  G  T  G  K  E  C  F  A  K  L  I  H  Q  H  S  T  R  Q  K  K  P  F  I  K  F  N  C  P  A  L  S  E
            H                                      S                                 H
            T I T      A                N     H    H N C                             T I                 B
            A N T      L                L     P    P C R                     H       A N                 B
            Q F H      U                A     H    A I F                     E       Q F                 V
            1 1 1      1                3     1    2 1 1                     3       1 1                 1
                                                     /
     AGCCTTCTCGAATCAGAGCTGTTTGGACATGAGAAAGGTGCGTTCACCGGGGCTATTGCTCAACGAGTAGGCCGTTTCGAATCGGCGAATGGCGGAACGT
1201 ----------+---------+---------+---------+---------+---------+---------+---------+---------+---------+ 1300
     TCGGAAGAGCTTAGTCTCGACAAACCTGTACTCTTTCCACGCAAGTGGCCCCGATAACGAGTTGCTCATCCGGCAAAGCTTAGCCGCTTACCGCCTTGCA

S  L  L  E  S  E  L  F  G  H  E  K  G  A  F  T  G  A  I  A  Q  R  V  G  R  F  E  S  A  N  G  G  T  L
       F                    H      S                            F                            H         F
       N     T               I     H N C                        M   N T                      H I        N
       U     A               N     P C R                        L   U T                      P N        U
       4     Q               F     A I F                        U   D H                      H F        4
       H     1               1     2 1 1                        1   2 2                      1 1        H
                                     //
     TGCTGCTCGATGAAATCGGCGAGATTCCCCCGGCGTTCCAAGCAAAACTGCTACGCGTAATACAGGAAGGTGAATTTGAGCGAGTCGGCGGCACAAAGAC
1301 ----------+---------+---------+---------+---------+---------+---------+---------+---------+---------+ 1400
     ACGACGAGCTACTTTAGCCGCTCTAAGGGGGCCGCAAGGTTCGTTTTGACGATGCGCATTATGTCCTTCCACTTAAACTCGCTCAGCCGCCGTGTTTCTG

L  L  D  E  I  G  E  I  P  P  A  F  Q  A  K  L  L  R  V  I  Q  E  G  E  F  E  R  V  G  G  T  K  T
              H H                                S           S
              H S A I T A G   A H                A X     T   A A                                  M
              G A C N A H I   A P                U H     A   V U                                  B
              A L C C Q A D   T A                3 0     Q   A 9                                  0
              1 1 1 2 1 2 1   2 2                A 2     1   2 6                                  2
                / /                                                /          /
     GCTGAAAGTCGACGTCCGGCTCATATTCGCCACAAATAAGGATCTCGAAATGGCGGTCCAGAATGGGGAGTTCAGGGAAGACCTTTACTACCGCATCAGC
1401 ----------+---------+---------+---------+---------+---------+---------+---------+---------+---------+ 1500
     CGACTTTCAGCTGCAGGCCGAGTATAAGCGGTGTTTATTCCTAGAGCTTTACCGCCAGGTCTTACCCCTCAAGTCCCTTCTGGAAATGATGGCGTAGTCG

L  K  V  D  V  R  L  I  F  A  T  N  K  D  L  E  M  A  V  Q  N  G  E  F  R  E  D  L  Y  Y  R  I  S
       S H        B              F              H        F                                                S
       F B G      S              M N     D M B  B G      N                H                             M A
       A A I      P              N U     D S G  A I      U                P                             B U
       N N C      1              L 4     E T L  N C      D                H                             0 3
       1 1 1      2              1 H     1 2 1  1 1      2                1                             2 A
        /                                 /         /
     GGGGTGCCCCTCATTTTGCCGCCCCTTAGGCACCGCGACGGTGACATTCCGCTCCTTGCAAGAGCATTCCTTCAGCGGTTCAACGAAGAGAACGGTCGTG
1501 ----------+---------+---------+---------+---------+---------+---------+---------+---------+---------+ 1600
     CCCCACGGGGAGTAAAACGGCGGGGAATCCGTGGCGCTGCCACTGTAAGGCGAGGAACGTTCTCGTAAGGAAGTCGCCAAGTTGCTTCTCTTGCCAGCAC

G  V  P  L  I  L  P  P  L  R  H  R  D  G  D  I  P  L  L  A  R  A  F  L  Q  R  F  N  E  E  N  G  R  D
                         F H          H                              B S        F
                         N I H        I H              T             S C        N N     A            M
                         U N H        N H              A             T R        U R     L            N
                         D P A        P A              Q             N F        D U     U            L
                         2 1 1        1 1              1             1 1        2 1     1            1
                           /                                                      /
     ATCTCCATTTCGCGCCGTCTGCGCTTGACCACTTGTCGAAGTGCAAGTTCCCTGGAAACGTTCGCGAGCTGGAAAACTGTGTGCGGAGGACTGCAACTCT
1601 ----------+---------+---------+---------+---------+---------+---------+---------+---------+---------+ 1700
     TAGAGGTAAAGCGCGGCAGACGCGAACTGGTGAACAGCTTCACGTTCAAGGGACCTTTGCAAGCGCTCGACCTTTTGACACACGCCTCCTGACGTTGAGA

L  H  F  A  P  S  A  L  D  H  L  S  K  C  K  F  P  G  N  V  R  E  L  E  N  C  V  R  R  T  A  T  L
             B S            S                         S
             S C            A                        A A     M                               M            N B H
             T R            U                        V U     B                               N          L A A
             N F            3                        A 9     0                               L          A L E
             1 1            A                        2 6     2                               1          3 1 3
               /                                       /                                                    /
     CGCCAGGTCAAAGACGATCACTTCGTCAGATTTCGCCTGCCAAACGGACCAGTGTTTTTCTTCTCGCCTCTGGAAAGGCGTTCACTGTTCGCATGGCCAC
1701 ----------+---------+---------+---------+---------+---------+---------+---------+---------+---------+ 1800
     GCGGTCCAGTTTCTGCTAGTGAAGCAGTCTAAAGCGGACGGTTTGCCTGGTCACAAAAAGAAGAGCGGAGACCTTTCCGCAAGTGACAAGCGTACCGGTG

```
     S   S        H      F                         H                           BB    SS                S
     F   A   CT   I H    NS   R                    I HH                        BSAHNFACX              F
     A   U   LA   N H    US   S                    N HA                        APMPCOURH              A
     N   3   AQ   P A    DT   A                    P AE                        N1HAIK3FO              N
     1   A   11   1 1    22   1                    1 12                        221211A12              1
                 /                                                                / // ///
       ATTGAGATCGATGCGCCCGCGGGTACAACACCGTTGCTCGGAGCGCCAGCCAATGACGTTCCGCCGAAAGAGCCCGGATCCGCAGGAGTGGCATCCAATC
1801   ---------+---------+---------+---------+---------+---------+---------+---------+---------+---------+ 1900
       TAACTCTAGCTACGCGGGCGCCCATGTTGTGGCAACGAGCCTCGCGGTCGGTTACTGCAAGGCGGCTTTCTCGGGCCTAGGCGTCCTCACCGTAGGTTAG

I  E  I  D  A  P  A  G  T  T  P  L  L  G  A  P  A  N  D  V  P  P  K  E  P  G  S  A  G  V  A  S  N  L

S         H F             S       H                H        F         S               S
       A   T     I NH    H       BA   M  MI  H           HH    I   N A       BT  F    M      HNC
       U   A     N UH    P       CU   N  NN  H           AP    N   U L       BA  A    N      PCR
       3   Q     P DA    A       L3   L  LP  A           EA    F   4 U       VQ  N    L      AIF
       A   1     1 21    2       1A   1  11  1           32    1   1 H 1     11  1    1      211
                 /                                                                             //
       TGATCGAGCGCGACCGGTTGATCAGTGCGCTGGAGGAGGCCGGTTGGAATCAGGCAAAGGCAGCTCGCATCCTCGAAAAAACGCCCCGGCAGGTCGGGCT
1901   ---------+---------+---------+---------+---------+---------+---------+---------+---------+---------+ 2000
       ACTAGCTCGCGCTGGCCAACTAGTCACGCGACCTCCTCCGGCCAACCTTAGTCCGTTTCCGTCGAGCGTAGGAGCTTTTTTGCGGGGCCGTCCAGCCCGA

I  E  R  D  R  L  I  S  A  L  E  E  A  G  W  N  Q  A  K  A  A  R  I  L  E  K  T  P  R  Q  V  G  L

F                           F                                    S
                    N           B    A  D   AN  H H          H H   NN                     M       T     F
                    L           B    L  D   LU  P G          G P   UR                     N       A     A
                    A           V    U  E   U4  A A          A H   DU                     L       Q     N
                    3           1    1  1   1H  2 1          1 1   21                     1       1 1   1
                                                                    /
       ATGCTCTACGTCGGCATGGTGTGGACGTGAGAAAGCTCTAAGCTGCCGGTGAGATAAAGCGTCGCGAGCGTCGCCTCTTTTCTCCGTCCTTTCGAAACAC
2001   ---------+---------+---------+---------+---------+---------+---------+---------+---------+---------+ 2100
       TACGAGATGCAGCCGTACCACACCTGCACTCTTTCGAGATTCGACGGCCACTCTATTTCGCAGCGCTCGCAGCGGAGAAAAGAGGCAGGAAAGCTTTGTG

C  S  T  S  A  W  C  G  R  E  K  A  L  S  C  R  *  D  K  A  S  R  A  S  P  L  F  S  V  L  S  K  H

H           F
              P           O
              A           K
              2           1
       GACCGGATGCAATTCAACTTTGCCCTT
2101   ---------+---------+------- 2127
       CTGGCCTACGTTAAGTTGAAACGGGAT

D  R  M  Q  F  N  F  A  L
```

Expression of a R.meliloti nifD::lacZ fusion by activation of the nifHDK promotor
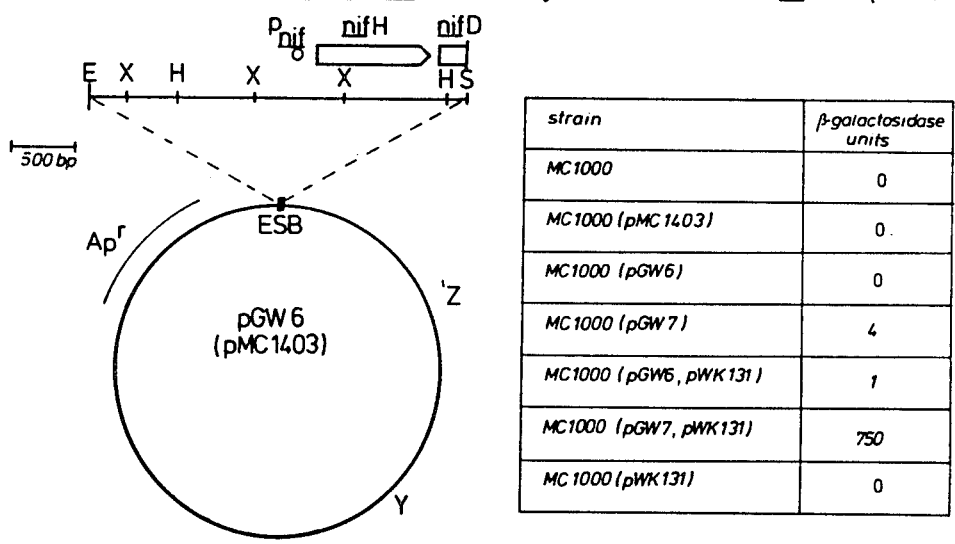
FIG. 6
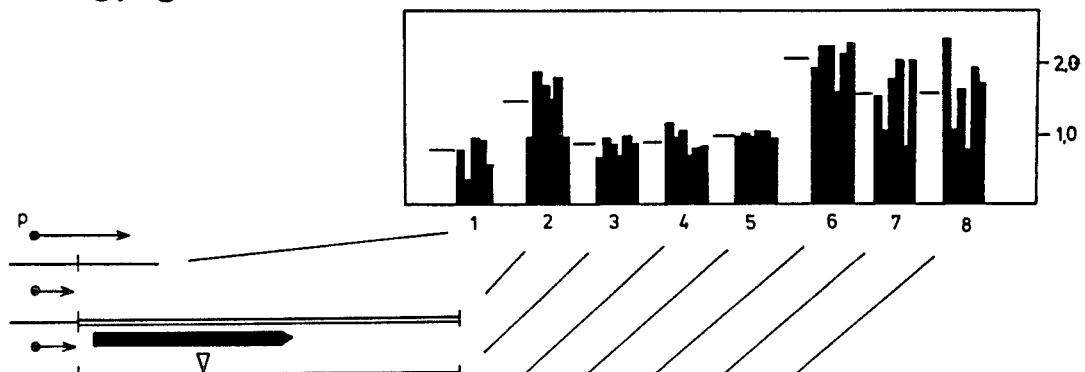
FIG. 7
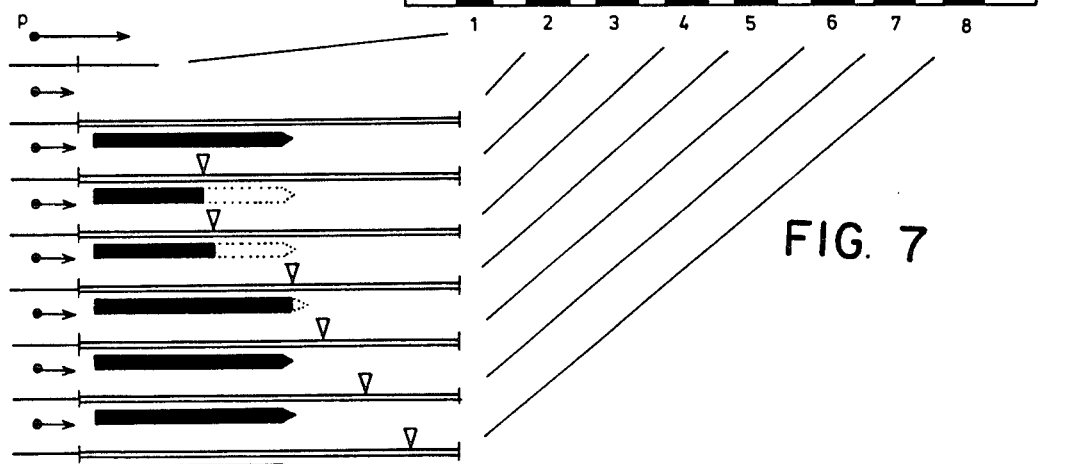
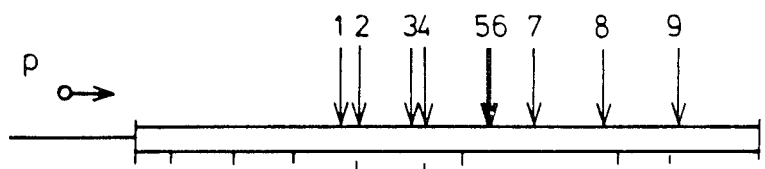
FIG. 8
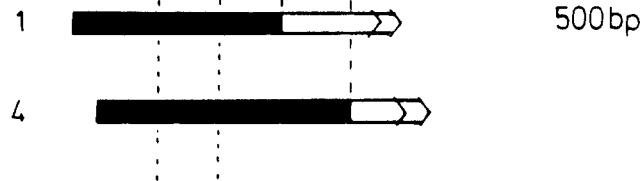

FIG. 10-1

Circular MAP of hrnifa.seq, check: 7581, from 1 to 2127.

HELMUT REILAENDER    ERSTE SEQUENZ
With enzymes: *

17-MAY-84  14:32

```
        H                    FH      F H           S
        I A                  NIH    M N I          HNCH                                              B                    F
        N L                  UNH    N U N          PCRA                                              B                    N       N
        D U                  DPA    L D F          AIFE                                              V                    U       L
        3 1                  211    1 2 1          2113                                              1                    4       A
                                                                                                                          H       3
      AAGCTTAAACCTGCCTCGCGCTCACGCGAGTCTTGCCCGGCCAAATGCTACGAGTTGAATGAAACTGGGCAAGTGGAAGTCACTGCCGATGGCTGCATGG
    1 ---------+---------+---------+---------+---------+---------+---------+---------+---------+---------+ 100
      TTCGAATTTGGACGGAGCGCGAGTGCGCTCAGAACGGGCCGGTTTACGATGCTCAACTTACTTTGACCCGTTCACCTTCAGTGACGGCTACCGACGTACC

K L K P A S R S R E S C P A K C Y E L N E T G Q V E V T A D G C M E

F                              H
            N       N       M              AG AT  H   MA                          M                    M
            U       L       N              HI AA  P   NL                          B                    N
            4       A       L              AD TQ  H   LU                          0                    L
            H       3       1              21 21  1   11                          2                    1
      AGTGCGGCACATGCAGAGTGTTGTGCGAGGCAAACGGTGACGTCGAGTGGAGCTATCCACGAGGTGGCTTCGGTGTCCTCTTCAAGTTCGGATGAGCCAC
  101 ---------+---------+---------+---------+---------+---------+---------+---------+---------+---------+ 200
      TCACGCCGTGTACGTCTCACAACACGCTCCGTTTGCCACTGCAGCTCACCTCGATAGGTGCTCCACCGAAGCCACAGGAGAAGTTCAAGCCTACTCGGTG

C G T C R V L C E A N G D V E W S Y P R G G F G V L F K F G * A T

H           S                          BS BS
        DF      T I         A     A                    SC AAX
        DO      A N         L     U                    TR MUH
        EK      Q F         U     3                    NF H3O
        11      1 1         1     A                    11 1A2
      TCTAAGGTCGATTCACAAGCTAGATCGGCGTTCAATAGGGGGACGAAGTGCCAGGGATCCTTACAAGAACCAACTTACCTTCCGTAACTTTATCGCTCTC
  201 ---------+---------+---------+---------+---------+---------+---------+---------+---------+---------+ 300
      AGATTCCAGCTAAGTGTTCGATCTAGCCGCAAGTTATCCCCCTGCTTCACGGTCCCTAGGAATGTTCTTGGTTGAATGGAAGGCATTGAAATAGCGAGAG

L R S I H K L D R R S I G G R S A R D P Y K N Q L T F R N F I A L

BH                       B
                             M                D         SG                      S           R
                             N                D         PI                      P           S
                             L                E         1A                      1           A
                             1                1         21                      2           1
      CGACTGTCAATACGCATACCTCCTAATATTAAGCGGGCGAGAAAATGACTAAGGTGCTCCCATCGCAACTCGTTCAGGGGAGTTAGTGCCCTGTCTGTAC
  301 ---------+---------+---------+---------+---------+---------+---------+---------+---------+---------+ 400
      GCTGACAGTTATGCGTATGGAGGATTATAATTCGCCCGCTCTTTTACTGATTCCACGAGGGTAGCGTTGAGCAAGTCCCCTCAATCACGGGACAGACATG

R L S I R I P P N I K R A R K * L R C S H R N S F R G V S A L S V P

H           H                                S
                   NIMH        I HHT                            AH
                   LNSH        N HAT                            UA
                   APTA        P AEH                            9E
                   3111        1 122                            63
      CTTCACAAAGAGACATGCGCAAACAGGACAAGCGCTCCGCCGAAATTTACAGCATATCAAAGGCTCTGATGGCCCCCACTCGTCTTGAGACCACGCTTAA
  401 ---------+---------+---------+---------+---------+---------+---------+---------+---------+---------+ 500
      GAAGTGTTTCTCTGTACGCGTTTGTCCTGTTCGCGAGGCGGCTTTAAATGTCGTATAGTTTCCGAGACTACCGGGGGTGAGCAGAACTCTGGTGCGAATT

S Q R D M R K Q D K R S A E I Y S I S K A L M A P T R L E T T L N

H      H    H F FF    H       H        H
                        IM     IMH  NISHN NNS I ATHX I          AG              F
                        NN     NSH  LNPHU UUS N VAGH N  H       HI              N
                        FL     PTA  APHA4 D4T F AQAO F  P       AD              U
                        11     111  3111H 2H2 1 1111 1  A       21              4
                                                        2                       H
      CAATTTCGTGAATACCCTCTCTTTGATTCTGCGCATGCGCCGCGGCGGACTCGAGATTCCGGCGTCGGAAGGAGAGACAAAGATAACAGCGGCTACCCGC
  501 ---------+---------+---------+---------+---------+---------+---------+---------+---------+---------+ 600
      GTTAAAGCACTTATGGGAGAGAAACTAAGACGCGTACGCGGCGCCGCCTGAGCTCTAAGGCCGCAGCCTTCCTCTCTGTTTCTATTGTCGCCGATGGGCG

```
                                  F                               S  F
         F                        N                               H  N
         N              R         N          T        N           N  N          R
         U              S         A          T        L           C  U          S
         4              A         U          H        A           P  4          A
         H              1         4          1        3           C  H          1
                                                                  R
                                  E                               A
                                  3                               I
                                  H                               F
                                                                  2
                                                                  1
                                                                  1
     AACAGCGGGTCTCCTTCTGCCGCTGATTATACTGTACCAAAGGCCGCAATAGACCAAGTCATGACTGCCGGGCGGCTGGTCGTACCAGACGTTTGCAACT
 601 ---------+---------+---------+---------+---------+---------+---------+---------+---------+---------+ 700
     TTGTCGCCCAGAGGAAGACGGCGACTAATATGACATGGTTTCCGGCGTTATCTGGTTCAGTACTGACGGCCCGCCGACCAGCATGGTCTGCAAACGTTGA

N  S  G  S  P  S  A  A  D  Y  T  V  P  K  A  A  I  D  Q  V  M  T  A  G  R  L  V  V  P  D  V  C  N  S

S              H F        S                 F  F              S
         D     A   A              I NH       A A        B      N  M  N           T A
         D     L   U              N U H      A V        B      M  N  U           A U
         E     U   3              P D A      A 9        V      4  L  4           Q 3
         1     1   A              1 2 1      2 6        1      H  1  H           1 A
     CTGAGCTGTTCAAGGATCAGATAAAATGGCGCGGAATTGGTCCGACTGCCTTCATCGCTGCGGCGGTGGAGGTCGATCACGAAACGGGCGGAATGCTGTG
 701 ---------+---------+---------+---------+---------+---------+---------+---------+---------+---------+ 800
     GACTCGACAAGTTCCTAGTCTATTTTACCGCGCCTTAACCAGGCTGACGGAAGTAGCGACGCCGCCACCTCCAGCTAGTGCTTTGCCCGCCTTACGACAC

E  L  F  K  D  Q  I  K  W  R  G  I  G  P  T  A  F  I  A  A  A  V  E  V  D  H  E  T  G  G  M  L  W

H        H                                            F              S
         T        I H      I         M M     M   M                R     H N     M      A   H
         A        N H      N         N B     N   N                S     A U     N      U   A
         Q        P A      F         L O     L   L                A     E 4     L      9   E
         1        1 1      1         1 2     1   1                1     3 H     1      6   3
     GTTCGAGTGCGCCGAAGAGTCCGATTATGATTATGAGGAGGAGGTACACTTTCTTTCTATGGCCGCCAATCTTGCGGGGAGGGCCATTCGGCTTCATCGC
 801 ---------+---------+---------+---------+---------+---------+---------+---------+---------+---------+ 900
     CAAGCTCACGCGGCTTCTCAGGCTAATACTAATACTCCTCCTCCATGTGAAAGAAAGATACCGGCGGTTAGAACGCCCCTCCCGGTAAGCCGAAGTAGCG

F  E  C  A  E  E  S  D  Y  D  Y  E  E  E  V  H  F  L  S  M  A  A  N  L  A  G  R  A  I  R  L  H  R

F          E
                                          N      M   C
                                          U      B   O                       B              F   F
                                          4      B   V                       B              N   N
                                          H      0   R                       V              U   U
                                                 2   1                       1              4   4
                                                                                             H   H
     ACAATCAGCAGGCGTGAGCGGACATTTGCCGAAGAGCAGCAAGAACAACAGAATTCACGTGATGAGCAGAGCCAGAGTTCCGCCCGCCAGCGGCTGCTCA
 901 ---------+---------+---------+---------+---------+---------+---------+---------+---------+---------+ 1000
     TGTTAGTCGTCCGCACTCGCCTGTAAACGGCTTCTCGTCGTTCTTGTTGTCTTAAGTGCACTACTCGTCGGTCTCAAGGCGGGCGGTCGCCGACGAGT

T  I  S  R  R  E  R  T  F  A  E  E  Q  Q  E  Q  Q  N  S  R  D  E  Q  S  Q  S  S  A  R  Q  R  L  L  K

S                                                  B
              A                     R          N    M             S  N                         D M
              U                     S          L    N             T  L                         D S
              3                     A          A    L             X  A                         E T
              A                     1          3    1             1  3                         1 2
     AGAATGACGGGATCATCGGGGAAAGTACCGCCCTCATGACGGCGGTAGATACCGCCAAAGTCATGGCAGAGACCAATTCAATCGTTCTCCTTAGGGGAGA
1001 ---------+---------+---------+---------+---------+---------+---------+---------+---------+---------+ 1100
     TCTTACTGCCCTAGTAGCCCCTTTCATGGCGGGAGTACTGCCGCCATCTATGGCGGTTTCAGTACCGTCTCTGGTTAAGTTAGCAAGAGGAATCCCCTCT

N  D  G  I  I  G  E  S  T  A  L  M  T  A  V  D  T  A  K  V  M  A  E  T  N  S  I  V  L  L  R  G  E

H                                     F H
                                    A                  T  I                                  N I H        D
                                    L                  A  N                                  U N H        D
                                    U                  Q  F                                  D P A        E
                                    1                  1  1                                  2 1 1        1
     AACAGGAACTGGCAAGGAATGCTTTGCGAAGCTAATCCACCAGCATTCGACTCGGCAAAAAAAGCCCTTCATCAAGTTCAATTGCCCCGCGCTGTCTGAG
1101 ---------+---------+---------+---------+---------+---------+---------+---------+---------+---------+ 1200
     TTGTCCTTGACCGTTCCTTACGAAACGCTTCGATTAGGTGGTCGTAAGCTGAGCCGTTTTTTTCGGGAAGTAGTTCAAGTTAACGGGGCGCGACAGACTC

T  G  T  G  K  E  C  F  A  K  L  I  H  Q  H  S  T  R  Q  K  K  P  F  I  K  F  N  C  P  A  L  S  E

H                                  S                     H
              T  I T         A              N    H      H N C           H     T  I        B
              A  N T         L              L    P      P C R           A     A  N        B
              Q  F H         U              A    H      A I F           E     Q  F        V
              1  1 1         1              3    1      2 1 1           3     1  1        1
     AGCCTTCTCGAATCAGAGCTGTTTGGACATGAGAAAGGTGCGTTCACCGGGGCTATTGCTCAACGAGTAGGCCGTTTCGAATCGGCGAATGGCGGAACGT
1201 ---------+---------+---------+---------+---------+---------+---------+---------+---------+---------+ 1300
     TCGGAAGAGCTTAGTCTCGACAAACCTGTACTCTTTCCACGCAAGTGGCCCCGATAACGAGTTGCTCATCCGGCAAAGCTTAGCCGCTTACCGCCTTGCA

```
       F                        H    S                       F                       H   F
       N  T                     I    HNC                  M  NT                      HI  N
       U  A                     N    PCR                  L  UT                      PN  U
       4  Q                     F    AIF                  U  DH                      HF  4
       H  1                     1    211                  1  22                      11  H
                                //
     TGCTGCTCGATGAAATCGGCGAGATTCCCCCGGCGTTCCAAGCAAAACTGCTACGCGTAATACAGGAAGGTGAATTTGAGCGAGTCGGCGGCACAAAGAC
1301 ---------+---------+---------+---------+---------+---------+---------+---------+---------+---------+ 1400
     ACGACGAGCTACTTTAGCCGCTCTAAGGGGGCCGCAAGGTTCGTTTTGACGATGCGCATTATGTCCTTCCACTTAAACTCGCTCAGCCGCCGTGTTTCTG

L  L  D  E  I  G  E  I  P  P  A  F  Q  A  K  L  L  R  V  I  Q  E  G  E  F  E  R  V  G  G  T  K  T

H  H                              S              S
                    HSAITAG AH                        AX    T        AA                                 M
                    GACNAHI AP                        UH    A        VU                                 B
                    ALCCQAD TA                        30    Q        A9                                 0
                    1112121 22                        A2    1        26                                 2
                      //                              /              /
     GCTGAAAGTCGACGTCCGGCTCATATTCGCCACAAATAAGGATCTCGAAATGGCGGTCCAGAATGGGGAGTTCAGGGAAGACCTTTACTACCGCATCAGC
1401 ---------+---------+---------+---------+---------+---------+---------+---------+---------+---------+ 1500
     CGACTTTCAGCTGCAGGCCGAGTATAAGCGGTGTTTATTCCTAGAGCTTTACCGCCAGGTCTTACCCCTCAAGTCCCTTCTGGAAATGATGGCGTAGTCG

L  K  V  D  V  R  L  I  F  A  T  N  K  D  L  E  M  A  V  Q  N  G  E  F  R  E  D  L  Y  Y  R  I  S

S H      B              F          H     F                                                       S
       FBG      S              MN      DMB BG   N                       H                             M A
       AAI      P              NU      DSG AI   U                       P                             B U
       NNC      1              L4      ETL NC   D                       H                             0 3
       111      2              1H      121 11   2                       1                             2 A
        /                                                                                               /
     GGGGTGCCCCTCATTTTGCCGCCCCTTAGGCACCGCGACGGTGACATTCCGCTCCTTGCAAGAGCATTCCTTCAGCGGTTCAACGAAGAGAACGGTCGTG
1501 ---------+---------+---------+---------+---------+---------+---------+---------+---------+---------+ 1600
     CCCCACGGGGAGTAAAACGGCGGGGAATCCGTGGCGCTGCCACTGTAAGGCGAGGAACGTTCTCGTAAGGAAGTCGCCAAGTTGCTTCTCTTGCCAGCAC

G  V  P  L  I  L  P  P  L  R  H  R  D  G  D  I  P  L  L  A  R  A  F  L  Q  R  F  N  E  E  N  G  R  D

FH      H                         BS       F
                        NIH     I H         T             SC       NN  A        M
                        UNH     N H         A             TR       UR  L        N
                        DPA     P A         Q             NF       DU  U        L
                        211     1 1         1             11       21  1        1
                         /                                /         /
     ATCTCCATTTCGCGCCGTCTGCGCTTGACCACTTGTCGAAGTGCAAGTTCCCTGGAAACGTTCGCGAGCTGGAAAACTGTGTGCGGAGGACTGCAACTCT
1601 ---------+---------+---------+---------+---------+---------+---------+---------+---------+---------+ 1700
     TAGAGGTAAAGCGCGGCAGACGCGAACTGGTGAACAGCTTCACGTTCAAGGGACCTTTGCAAGCGCTCGACCTTTTGACACACGCCTCCTGACGTTGAGA

L  H  F  A  P  S  A  L  D  H  L  S  K  C  K  F  P  G  N  V  R  E  L  E  N  C  V  R  R  T  A  T  L

BS         S                          S                              M              N  BH
       SC         A                          AA    M                        N              L  AA
       TR         U                          VU    B                        L              A  LE
       NF         3                          A9    0                        1              3  13
       11         A                          26    2
        /                                     /                                              /
     CGCCAGGTCAAAGACGATCACTTCGTCAGATTTCGCCTGCCAAACGGACCAGTGTTTTTCTTCTCGCCTCTGGAAAGGCGTTCACTGTTCGCATGGCCAC
1701 ---------+---------+---------+---------+---------+---------+---------+---------+---------+---------+ 1800
     GCGGTCCAGTTTCTGCTAGTGAAGCAGTCTAAAGCGGACGGTTTGCCTGGTCACAAAAAGAAGAGCGGAGACCTTTCCGCAAGTGACAAGCGTACCGGTG

A  R  S  K  T  I  T  S  S  D  F  A  C  Q  T  D  Q  C  F  S  S  R  L  W  K  G  V  H  C  S  H  G  H

S  S           H     F                  H                             BB    SS                   S
       F  A      CT   I H   NS   R             I HH                          BSAHNFACX                  F
       A  U      LA   N H   US   S             N HA                          APMPCOURH                  A
       N  3      AQ   P A   DT   A             P AE                          N1HAIK3FO                  N
       1  A      11   1 1   22   1             1 12                          221211A12                  1
           /                                                                   / // ///
     ATTGAGATCGATGCGCCCGCGGGTACAACACCGTTGCTCGGAGCGCCAGCCAATGACGTTCCGCCGAAAAGAGCCCGGATCCGCAGGAGTGGCATCCAATC
1801 ---------+---------+---------+---------+---------+---------+---------+---------+---------+---------+ 1900
     TAACTCTAGCTACGCGGGCGCCCATGTTGTGGCAACGAGCCTCGCGGTCGGTTACTGCAAGGCGGCTTTCTCGGGCCTAGGCGTCCTCACCGTAGGTTAG

I  E  I  D  A  P  A  G  T  T  P  L  L  G  A  P  A  N  D  V  P  P  K  E  P  G  S  A  G  V  A  S  N  L

S         H F          S         H                H           F          S              S
       A    T    I NH   H     BA   M    MI H             HH     I    N  A       BT  F    M    HNC
       U    A    N UH   P     CU   N    NN H             AP     N    U  L       BA  A    N    PCR
       3    Q    P DA   A     L3   L    LP A             EA     F    4  U       ·VQ N    L    AIF
       A    1    1 21   2     1A   1    11 1             32     1    1  H1      11  1    1    211
        /                                                                                       //
     TGATCGAGCGCGACCGGTTGATCAGTGCGCTGGAGGAGGCCGGTTGGAATCAGGCAAAGGCAGCTCGCATCCTCGAAAAAACGCCCCGGCAGGTCGGGCT
1901 ---------+---------+---------+---------+---------+---------+---------+---------+---------+---------+ 2000
     ACTAGCTCGCGCTGGCCAACTAGTCACGCGACCTCCTCCGGCCAACCTTAGTCCGTTTCCGTCGAGCGTAGGAGCTTTTTGCGGGGCCGTCCAGCCCGA

ATGCTCTACGTCGGCATGGTGTGGACGTGAGAAAGCTCTAAGCTGCCGGTGAGATAAAGCGTCGCGAGCGTCGCCTCTTTTCTCCGTCCTTTCGAAACAC
2001 ---------+---------+---------+---------+---------+---------+---------+---------+---------+---------+ 2100
     TACGAGATGCAGCCGTACCACACCTGCACTCTTTCGAGATTCGACGGCCACTCTATTTCGCAGCGCTCGCAGCGGAGAAAAGAGGCAGGAAAGCTTTGTG

C  S  T  S  A  W  C  G  R  E  K  A  L  S  C  R  *  D  K  A  S  R  A  S  P  L  F  S  V  L  S  K  H

H            F
          P            O
          A            K
          2            1

GACCGGATGCAATTCAACTTTGCCCTT
2101 ---------+---------+------- 2127
     CTGGCCTACGTTAAGTTGAAACGGGAT

FIG. 12 fixD-promoter

FIG. 15

```
———— PROMOTER REGION ————
              PvuII
1401 ACAGCCAAGCGAACCGGAATTGCCAGCTGGGGCGCCCTCTGGTAAGGTTGGGAAGCCCTGCAAAGTAAACTGGATGGCTTTCTTGCCGCCAAGGATCTGAT
          BglII BclI
1501 GGCCAGGGGATCAAGATCTGATCAAGAGACAGGATGAGGATCGTTTCCCATGATTGAACAAGATGGATTGCACGCAGGTTCTCCGCCGCTTGGGTGGA
                             PstI                       BalI            MstI PvuII
1601 GAGGCTATTCGGCTATGACTGGGCACAACAGACAATCGGCTGCTCTGATGCCGCCGTGTTCCGGCTGTCAGGCGCAGGGGCGCCCGGTTCTTTTTGTCAAG
1701 ACCGACCTGTCCGGTGCCCTGAATGAACTGCAGGACGAGGCAGGCGGCTATCGTGGCTGGCCACGACGGGCGTTCCTTGCCGAGCTGTCTCGACGTTG
                                                                                SphI
1801 TCACTGAAGCGGGAAGGGACTGGCTGCTATTGGGCGAAGTGCCGGGCAGGATCTCCTGTCATCTCACCTTGCTCCTGCCGAGAAAGTATCCATCATGGC
1901 TGATGCAATGCGGCGGCTGCATACGCTTGATCGGCTACCTGCCATTCGACCACCAAGCGAAACATCGCATCGAGCGAGCACGTACTCGGATGGAAGCC
2001 GGTCTTGTCGATCAGGATGATCTGGACGAAGAGCATCAGGGGCTCGCGCCAGCCAACTGTTCGCCAGGCTCAAGGCGCGCATGCCCGACGGCGAGGATC
                                                                                                      SphI
2101 TCGTCGTGACCCATGGCGATGCCTGCTTGCCGAATATCATGGTGGAAAATGGCCGCTTTTCTGGATTCATCATCGACTGTGGCCGGCTGGTGTGGCGGACCG
2201 CTATCAGGACATAGCGTTGGCTACCCGTGATATTGCTGAAGAGCTTGGCGGCGAATGGGCTGACCGCTTCCTCGTGCTTTACGGTATCGCCGCTCCCGAT
2301 TCGCAGCGCATCGCCTTCTATCGCCTTCTTGACGAGTTCTTCTGAGCGGGACTCTGGGGTTCGAAATGACCGACCAAGCGACGCCCAACCTGCCATCACG
2401 AGATTTCGATTCCACCGCCGCCTTCTATGAAAGGTTGGGCTTCGGAATCGTTTCCGGACGCCGCCGGCTGGATGATCTCCAGCGCGGGGATCTCATGCTG
                                         PvuII
2501 GAGTTCTTCGCCCACCCCGGGCTCGATCCCCTCGCGAGTTGGTTCAGCTGCTGCCTGAGGCTGGACGACCTCGGAGTTCTACCGGCAGTGCAAATCCG
                                                                                               SalI
2601 TCGGCATCCAGGAAACCAGCAGCGGCTATCCGCGCATCCATGCCCCGAACTGCAGGAGTGGGGAGGCACGATGGCCGCTTGGTCGACCCGGACGGGAC
```

NITROGEN FIXATION REGULATOR GENES

CROSS REFERENCE TO RELATED APPLICATION

This is a continuation-in-part of U.S. Ser. No. 616,586, filed June 4, 1984, now abandoned.

FIELD OF THE INVENTION

Biological nitrogen fixation in the root nodules of leguminous plants is a major component of world food production and therefore practical applications of this field are of major interest.

Prokaryotes can use a wide variety of nitrogen compounds as sole sources of cellular nitrogen. This variety includes ammonia, dinitrogen and nitrate among the inorganic compounds, and proline, arginine and glutamine among complex organic compounds. Each species can utilize a different array of nitrogen compounds. Glutamine, glutamate and aspartate are the key nitrogen compounds in intermediary metabolism. The latter two are the starting compounds of many pathways of amino acid biosynthesis and serve as amino group donors in many reactions. In all other cases the amino group is donated by glutamine. The major enzyme required for the assimilation of ammonia produced by $N_2$ fixation is glutamine synthetase, which catalyses the reaction:

Glutamate + $NH_3$ + ATP → glutamine + ADP + Pi.

At high $NH_4^+$ concentrations (>1 mM) glutamate dehydrogenase is also found. Utilization of the assimilated ammonia depends on the activity of glutamate synthase catalyzing:

Glutamine + 2-ketoglutarate + NADPH → 2 glutamate + $NADP^+$

Since ATP is hydrolysed, these reactions have a favorable equilibrium and allow the use of ammonia in the medium or ammonia derived enzymatically from other nitrogen sources (Meers, J., Tempest, D. and C. Brown (1970) J. Gen. Microbiol. 64: 187–194). The formation of ammonia is thus a key step in the biological nitrogen cycle.

Biological nitrogen fixation can be achieved by a variety of microorganisms and occurs through the induction of an enzyme complex, nitrogenase, which converts atmospheric nitrogen to ammonia. This conversion occurs in a group of physiologically diverse prokaryotes, including facultative anaerobes (e.g., *Klebsiella pneumoniae* and *Rhodospirillum rubrum*), obligate anaerobes (e.g., *Clostridium pasteurianum*), obligate aerobes (e.g., *Azotobacter vinelandii*) and some strains of blue-green algae (e.g., *Anabaena cylindrica*) (Sprent, J. I. (1979) *The biology of nitrogen fixing organisms*, London, McGraw-Hill, pp. 8–11). While this enzyme complex is common to all characterized nitrogen fixing organisms, the conditions under which it is expressed vary considerably between species (Burns, R. C., Hardy, R. W. F. (1975): Nitrogen fixation in bacteria and higher plants, Springer-Verlag, Berlin). The first stages of nitrogen fixation, conversion of nitrogen into ammonia, are achieved symbiotically in the root nodules of leguminous plants which contain the nitrogen-fixing bacteria of the genus Rhizobium. Some non-leguminous plants, e.g., alder, also have interactions with symbiotic bacteria which are nitrogen fixers. In addition, free-living bacteria, e.g., *Klebsiella pneumoniae* and the photosynthetic blue-green bacteria, also fix nitrogen. Biological nitrogen fixation in the root nodules of leguminous plants is a major component of world food production (Burris, R. H. (1980) In *Free Living Systems and Chemical Models; Nitrogen fixation*, Newton, W. E., Orme-Johnson, W. H., eds. Vol 1 Baltimore, University Park Press, pp. 7–16).

The symbiotic association between plants and bacteria of the genus Rhizobium is the result of a complex interaction between the bacterium and its host, requiring the expression of both bacterial and plant genes in a tightly coordinated manner (Vincent, J. M. (1980) In *Symbiotic Associations and Cyanobacteria, Nitrogen Fixation* Vol. 2 (W. E. Newton, W. H. Orne-Johnson, eds.) Baltimore, University Park Press pp. 103–129; and Verma, D. P. S., Legocki, R. P. and S. Auger (1981) In *Current Perspectives in Nitrogen Fixation* (A. H. Gibson, W. E. Newton, eds.) Canberra: Australian Academy of Science, pp. 205–208). In free-living Rhizobia, nitrogenase synthesis is repressed and is only induced after the symbiotic relationship has been established. Furthermore, some Rhizobium species only interact with a narrow range of plant species, whereas other species interact with a wide range.

Bacteria bind to the emerging plant root hairs and invade the root tissue through the formation of an infection thread. The plant responds to this infection by the development of a highly differentiated root nodule. These nodules are the site of synthesis of the nitrogenase complex. Following nitrogen fixation, the fixed nitrogen is exported into the plant tissue and assimilated by the plant derived enzymes (Scott, D. B., Farnden, K. J. F. and Robertson, J. G. (1976) Nature 263: 703,705).

Most Rhizobium symbioses are confined to leguminous plants. Furthermore, Rhizobium strains which fix nitrogen in association with the agriculturally-important temperate legumes are usually restricted in their host range to a single legume genus. However, some strains of Rhizobium have been isolated which can fix nitrogen in a diverse group of legume species but can also form an effective symbiosis with non-legumes.

Despite the ability of certain plants to induce nitrogenase activity in a symbiotic relationship with some species of Rhizobium, the genetic analysis of biological nitrogen fixation has previously been confined to free living nitrogen fixing organisms, in particular *Klebsiella pneumoniae*. There are 17 linked nitrogen fixation (nif) genes arranged in at least 7 transcriptional units in the nif cluster of Klebsiella (Kennedy, C., Cannon, F., Cannon, M., Dixon, R., Hill, S., Jensen, J., Kumar, S., McLean, P., Merrick, M., Robson, R. and Postgate, J. (1981) In *Current Perspectives in Nitrogen Fixation* (A. H. Gibson, W. E. Newton, eds.) Canberra: Australian Academy of Science, pp. 146–156; and Reidel, G. E., Ausubel, F. M. and F. M. Cannon (1979) Proc. Nat. Acad. Sci. U.S.A. 76: 2866–2870). Three of these genes, nifH, nifD and nifK encode the structural proteins of the nitrogenase enzyme complex (viz. the Fe-protein subunit (dinitrogenase reductase) and the $\alpha$- and $\beta$-subunits of the Mo-Fe protein (dinitrogenase) respectively. Dinitrogenase is an $\alpha_2\beta_2$ tetramer in which the two non-identical $\alpha$ and $\beta$ subunits have similar molecular weights of 55,000 to 60,000. Dinitrogenase reductase is a dimer of two identical subunits each having a molecular weight around 35,000. These genes are linked on the same operon in *K. pneumoniae* and are transcribed from a promoter adjacent to the nifH gene. A similar situation (nifHDK) was found in two fast-growing Rhizobia, *R. meliloti* (Ruvkun, G. B., et al. (1982) Cell 29: 551–559) and *R. leguminosarum* (Schetgens, T. M. P. et al. (1984) Identification and analysis of the expression of *Rhizobium leguminosarum* PRE symbiotic genes, p. 699, In C. Veeger and W. E. Newton (eds.) Advances in nitrogen fixation research. Martinus Nijhoff/Dr. W. Junk Publishers, The Hague). In the slow-growing *R. japonicum*, it has been found that nifDK forms one operon and that nifH is located elsewhere on the genome (Fuhrmann, M. and H. Hennecke (1982) Mol. Gen. Genet. 187: 419–425). A similar observation was made with another member of the slow-growing rhizobia, Rhizobium sp. Parasponia: a nifH region was found not to be linked to nifD (Scott, K. F., et al. (1983) DNA 2: 141–148).. Yet a different arrangement was detected in the cyanobacterium Anabaena sp. 7120, in which nifHD is separated from nifK (Rice, D., et al. (1982) J. Biol. Chem. 257: 13157–13163). The remainder of symbiotic genes contain information required for bacterial attachment, root hair curling, initiation and development of nodules and establishment of symbiotic relationships. In addition, regulatory sequences such as promoters, operators, attenuators, and ribosome binding sites are found adjacent to the coding regions. These regulatory sequences control the expression of the structural genes, i.e., the coding sequences downstream in the 3'-direction of the DNA reading strand.

The discovery and study of plasmids, restriction enzymes, ligases and other enzymes involved in DNA synthesis has led to the rapidly developing field of genetic engineering. Use of these techniques has made it possible to transfer DNA across species boundaries, either from eukaryotic to prokaryotic organisms or vice versa. Alternatively, it has been possible to synthesize nucleotide sequences and to incorporate these synthetic sequences into living organisms where they have been expressed. For example, expression in *E. coli* has been obtained with DNA sequences coding for mouse dihydrofolate reductase (Chang, A. C. Y., Nunberg, J. H., Kaufman, R. K., Ehrlich, H. A., Schimke, R. T. and Cohen, S. N. (1978) Nature 275: 617–624) and for hepatitis B virus antigen (Burrell, C. J., Mackay, P., Greenaway, P. J., Hofschneider, P. H. and K. Murray (1979) Nature 279: 43–47). Two mammal hormones have also been produced in bacteria by use of synthetic DNA (Itakura, K., Hirose, T., Crea, R., Riggs, A. D., Heynecker, H. L., Bolivar, F., and H. W. Boyer (1977) Science 198: 1056; and Goeddel, D. B., Kleid, D. G., Bolivar, F., Heynecker, H. L., Yansura, D. G., Crea, R., Hirose, T., Kraszewski, A., Itakura, K. and A. D. Riggs (1979) Proc. Nat. Acad. Sci. U.S.A. 76: 106).

The practical application of DNA recombination requires the success of a number of different features. First, it must be possible to recognize the DNA fragment coding for the compound of interest and it must be possible to isolate that DNA fragment. Second, it is necessary to understand the mechanisms which control the expression of the information on that DNA fragment and to be able to transfer that information to the control of regulatory sequences which will maximize the productive capabilities of that information. This increased productive capacity could be by rearrangement of coding information and regulatory information within the same organism or between different organisms. The organisms involved may be prokaryotic or eukaryotic. Third, the conversion of coding information into useful products, such as storage proteins and hormones, must occur in an environment where they are not subsequently degraded.

BACKGROUND OF THE INVENTION

In bacteria of the genus Rhizobium, nitrogenase synthesis is normally repressed under free-living conditions and is induced only within a complex symbiosis formed mostly with leguminous plants. *R. trifolii* is an example of a fast-growing Rhizobium with a narrow host range and cannot normally be induced to fix nitrogen in culture. In contrast, a Parasponia Rhizobium species has been isolated and this species is a slow-growing organism with a very broad host range capable of an effective symbiotic relationship with a broad variety of tropical legumes as well as the non-legume Parasponia (Ulmaceae) (Trinick, M. J. (1980) J. Appl. Bacteriol. 49: 39–53). *Parasponia Rhizobium* can be induced to fix nitrogen in culture although the level of this fixation is about 100-fold less than can be obtained from the free-living bacterium *Klebsiella pneumoniae*. Other slow-growing Rhizobia include the commercially significant *R. japonicum*, which nodulates soybeans.

The genetics of biological nitrogen fixation have been well characterized in the free-living organism *Klebsiella pneumoniae*. The structural genes for nitrogenase (nifH, nifD and nifK encoding the Fe-protein subunit and the $\alpha$ and $\beta$ subunits of the Mo-Fe protein, respectively) have been mapped both genetically and physically (Kennedy, C. et al. (1981) In *Current Perspectives in Nitrogen Fixation* (eds. Gibson, A. H. and W. E. Newton) Australian Acad. Science, Canberra, pp. 146–156; and Reidel, G. E., Ausubel, F. M. and F. M. Cannon (1979) Proc. Nat. Acad. Sci. U.S.A. 76: 2866–2870). Cloned DNA fragments carrying these sequences have been shown, by Southern blot analysis, to hybridize to homolgous sequences in a wide range of nitrogen fixing organisms, including Rhizobium (Ruvkun, G. B. and F. M. Ausubel (1980) Proc. Nat. Acad. Sci. U.S.A. 77: 191–195).

In spite of the ecological diversity of nitrogen fixing organisms, the physiological structure of the nitrogenase enzyme complex appears to be very conserved. In all cases where the enzyme complex has been purified, two proteins are present. The larger protein (dinitrogenase) contains molybdenum, iron and acid-labile sulfur, and carries the binding site for nitrogen and contains two subunit proteins $\alpha$- and $\beta$-coded by the nifD and nifK genes respectively. The smaller protein (dinitrogenase reductase) contains iron and acid-labile sulfur, and is required for the reduction of the dinitrogenase and for the binding of MgATP used in this reduction. The dinitrogenase reductase is coded by the nifH gene. Chemical and spectral analyses of the purified protein components support a conservation of protein structure between organisms (Scott, K. F., Rolfe, B. G. and J. Shine (1981) J. Mol. Appl. Genet. 1: 71–81). In some cases the structures are sufficiently similar to allow formation of active hybrid enzymes between purified components, e.g., *Azotobacter vinelandii* and *Klebsiella pneumoniae* (Eady, R. R. and B. E. Smith (1979) In: *A treatise on dinitrogen fixation* I, II, eds. Hardy, R. W., Bottomley, F. and R. C. Burns, New York, Wiley Press pp. 399–490). Not surprisingly, therefore, the region of the nif operon coding for dinitrogenase reductase and dinitrogenase $\alpha$-subunit (nifH and nifD) shows homology at the nucleic acid sequence level with the corresponding sequences in at least 19 other bacterial strains (Ruvkun, G. B. and F. M. Ausubel (1980) Proc. Nat. Acad. Sci.

U.S.A. 77: 191–195). Although this conservation of structure is generally true, significant differences between nitrogenases from different organisms also exist as can be shown by variable stability following purification and by the fact that active hybrid complexes do not form in all cases (Eady, R. R. and B. E. Smith (1979) supra).

A DNA fragment carrying the *Klebsiella pneumoniae* nifK, nifD and nifH genes has been isolated from the nif strain UNF841(Tn5::nifK) (Cannon, F. C. et al. (1979) Mol. Gen. Genet. 174: 59–66) and cloned into the *Escherichia coli* plasmid pBR325. The nucleotide sequences of the nifH gene and of 622 nucleotides of the nifD gene were determined (Sundaresan, V. and F. M. Ausubel (1981) J. Biol. Chem. 256: 2808–2812; Scott, K. F., Rolfe, B. G. and J. Shine (1981) supra). In addition, the DNA sequence of the nifH gene from Anabaena 7120 has been determined (Mevarech, M., Rice, D. and R. Haselkorn (1980) Proc. Nat. Acad. Sci. U.S.A. 77: 6476–6480). A comparison of the two sequences demonstrates two interesting features: (1) There is very little homology between the two sequences at the nucleotide sequence level although a few stretches (up to 25 bp) are conserved, accounting for the observed interspecies homology of the nif genes (Ruvkun, G. B. and F. M. Ausubel (1980) supra); (2) In general, the promoter regions show very little sequence homology with the exception of a short region likely to be involved in common functions, e.g., RNA polymerase recognition.

In contrast, a comparison of the amino acid sequences of the dinitrogenase reductase and of the first 207 amino acids of the α-subunit of dinitrogenase of the two species and of another species show a much greater conservatism. The three species used in this comparison are *Klebsiella pneumoniae* (Kp); Anabaena 7120 (Ab); and *Clostridium pasteurianum* (Cp) (Tanaka, M., Haniu, M., Yasunobu, T. and L. Mortenson (1977) J. Biol. Chem. 252: 7093–7100). The Kp and Cp proteins share 67% amino acid sequence homology, Kp and Ab proteins share 71% homology, and the Cp and Ab proteins share 63%. This amino acid sequence homology is not spead evenly throughout the protein. Some regions are virtually identical—90% to 95% homology), while other regions are only weakly conserved (30–35% homology). The structural conservation appears to be centered around the five cysteine residues common to all three Fe proteins. These cysteine residues are believed to be ligands to the active center.

Comparison of the N-terminal amino acid sequence of the α-subunit of dinitrogenase from Cp and Kp shows very little sequence homology in this region. This is in contrast to the very high conservation of amino acid sequence seen in the amino terminal region of the Fe protein. What little homology exists between Cp and Kp α-subunits is confined to regions around cysteine residues, as in the Fe proteins. These homologous regions are thought to be involved in the catalytic functions of the nitrogenase enzyme complex. Therefore, this structural conservatism is thought not to be the result of recent evolution and dispersal of the nif genes (Postgate, J. R. (1974) Sym. Soc. Gen. Microbiol. 24: 263–292) but, rather, is postulated to be related to a conservation of function.

The isolation of *Klebsiella pneumoniae* DNA which codes for the structural genes of the nitrogenase complex (Ruvkun, G. B. and Ausubel, F. M. (1980) Proc. Nat. Acad. Sci. USA 77: 191–195) has facilitated the identification of the corresponding structural genes of *Rhizobium meliloti*. The *R. meliloti* genes were found on an EcoRI fragment which was cloned in *E. coli* plasmid vectors (Ruvkun, G. B. and F. M. Ausubel (1981) Nature 289: 85–88). Further studies using fragment specific mutagenesis in *E. coli* and transfer of the mutations to the *R. meliloti* genome confirmed that the cloned fragment carries nif specific genes (Ruvkun, G. B. et al. (1980) Cold Spring Harb. Symp. Quant. Biol. 45: 492–497; Ruvkun, G. B. et al. (1982) Cell 29: 551–559). This cloned *R. meliloti* fragment has been analysed by the minicell technique and it was demonstrated that the nifH gene of *R. meliloti* was expressed in minicells of *E. coli* (Weber, G. and A. Puhler (1982) Plant Mol. Biol. 1: 305–320). In free living *R. meliloti*, the nifH gene is not expressed. Further experiments have identified a number of *R. meliloti* genes involved in symbiotic nitrogen fixation and a preliminary map of *R. meliloti* nif and fix genes was published (Puhler, A. et al. (1983) In: Advances in Nitrogen Fixation Research (ed. by Veeger, Newton). The Hague, Boston, Lancaster). This map contains the coding regions of the following *R. meliloti* genes nifK, nifH, nifD, fixA, fixB and fixC (FIG. 1). This figure gives a preliminary restriction map of the *Rhizobium meliloti* nif and fix genes and their promoters. In addition, the coding regions of the various nif and fix genes are shown by black arrows. The direction of transcription and translation is also shown by the arrows. nifK and nifD are presented as hybrid genes. The indicated promoters (p) were identified in *E. coli*. The nifH as well as the fixA promoter can be activated by the *K. pneumoniae* nifAgp protein. The abbreviations used in the restriction map are: C, ClaI; E, EcoRI; H, HindIII; P, PstI; S, SmaI; and X, XhoI.

Of special interest is the transcriptional regulation of the *R. meliloti* fix/nif region. In FIG. 1, two promoters are indicated; one is located next to nifH and the other is next to fixA. For both the nifH promoter and the fixA promoter it has been demonstrated that they can be activated in *E. coli* by the Klebsiella nifA gene product (Puhler, A. et al. (1983) see supra). The nifH and the fixA promoter are reading in opposite directions. Sundaresan, V. et al. [(1983) Nature 301: 728–732] and Sundaresan, V. et al. [(1983) Proc. Nat. Acad. Sci. USA 80: 4030–4034] identified and sequenced the nifH promoter and found some homology to the *K. pneumoniae* nifH promoter. Corbin, D. et al. [(1983) Proc. Nat. Acad. Sci. USA 80: 3005–3009] also identified the fixA promoter as well as the nifH promoter of *R. meliloti*. In contrast, the *K. pneumoniae* nifH promoter cannot be activated by the *E. coli* glnG gene product, whereas the *R. meliloti* nifH promoter can be activated by the *E. coli* glnG gene product. These observations imply that the activator and/or the promoter of nifH in *Klebsiella pneumoniae* and *Rhizobium meliloti* are different. Indeed, no endogenous activator of the nifH and fixA genes of *R. meliloti* was known.

SUMMARY OF THE INVENTION

The isolation and characterization of a gene which activates nitrogen fixing genes of *Rhizobium meliloti* when that bacterium is in a symbiotic relationship with a plant is described. A method of altering the nature of this gene from an inducible state to a constitutive state is presented. In addition, it is possible to combine the promoter of the activating gene with the coding regions of other genes. This recombination is useful when the expression of that gene is only desirable during a symbiotic relationship between the bacterium and the plant.

In particular, a recombinant DNA plasmid comprising a vector, a promoter of a gene of a Rhizobium species, wherein said gene codes for a product normally capable of activating nitrogen fixation, and a foreign structural gene or foreign DNA fragment under control of said promoter is disclosed. Also disclosed is a recombinant DNA plasmid comprising a vector, a promoter of a constitutively expressed gene, and a coding sequence of a gene which codes for a product capable of activating nitrogen fixation. Bacterial strains containing and replicating such plasmids are also disclosed. Furthermore, a method is taught for activating expression of nitrogen fixation genes by placing said nitrogen fixation genes under control of a genetically manipulated consititutively expressed activating gene comprising the steps of combining a promoter of a constitutive gene in such a position as to control an activating gene thereby producing a constitutive expression of the activating gene, transforming a strain of *Escherichia coli* with a constitutive gene transfer system comprising a suicide vector and a transposon wherein the constitutively expressed activating gene is inserted within the transposon, transferring said consitutive gene transfer system to a strain of gram-negative bacteria having said nitrogen fixation genes, and selecting a recombinant strain of said gram-negative bacteria wherein said constitutively expressed activating gene is contained, replicated and expressed in said gram-negative bacteria, thereby activating fixation of dinitrogen by activating expression of said nitrogen fixation genes.

BRIEF DESCRIPTION OF THE DRAWINGS

IN FIGS. 1, 2, 4, 8, and 11, restriction sites are indicated as follows: B, BamHI; Bg, BglII; C, ClaI; E, EcoRI; H, HindIII; P, PstI; S, SmaI; and X, XhoI. FIGS. 1, 2, 14, and 15 have been previously published and are presented herein for the convenience of those in the art.

FIG. 1 reproduces a preliminary map of *R. meliloti* nif and fix genes published by Puhler A et al. (1983) in: *Advances in Nitrogen Fixation Research* (ed. by Veeger N).

FIG. 2 reproduces the coding regions of the *K. pneumoniae* nifA and nifL genes, shown in relation to their restriction map, as published by Puhler A and Klipp W (1981) in: *Biology of Inorganic Nitrogen and Sulfur*; eds. Bothe H and Trebst A.

FIG. 3 presents Southern blot analysis of *R. meliloti* plasmids pRmW54, pRmR3, and pRmW52. FIG. 3a is a photograph of stained DNA. FIG. 3b is an autoradiograph of the DNAs of FIG. 3a probed with *K. pneumoniae* nifA sequences. FIG. 3c is an autoradiograph of these DNAs probed with *K. pneumoniae* nifL.

FIG. 4 presents a restriction map of the *R. melioti* fix gene region which interprets data presented in FIG. 3.

FIG. 5 presents sequence, restriction sites, and encoded protein of the *R. meliloti* fixD.

FIG. 6 presents a map of plasmid pGW6 and results of activation of a *R. meliloti* nifD::lacZ fusion by the *K. pneumoniae* nifA gene product (Example 2).

FIG. 7 presented the activation of the *Rhizobium meliloti* nifH promoter in pGW7 by the fixD gene product of *R. meliloti* (Example 2).

FIG. 8 presents the restriction map of the HindIII fragment from pRmR29D5 and the positions of the several Tn5 insertions.

FIG. 10 represents the sequence of the fixD gene (Example 1).

FIG. 11 presents an overall map of the fix and nif genes (Example 1).

FIG. 12 diagrams the preparation of a blunt-ended DNA fragment having the fixD promoter (fixD-P) (Example 3).

FIG. 13 diagrams placement of the fixD promoter-bearing EcoRI fragment in a vector capable of propagating that fragment (Example 3).

FIG. 14 diagrams pSUP1011.

FIG. 15 reproduces the sequence of the neomycin phosphotransferase (kan) gene, as published by Beck E et al. (1982) Gene 19: 327–336.

DETAILED DESCRIPTION OF THE INVENTION

Figure 1:
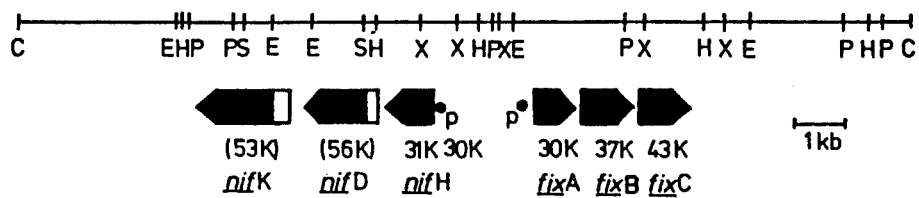
Figure 2:
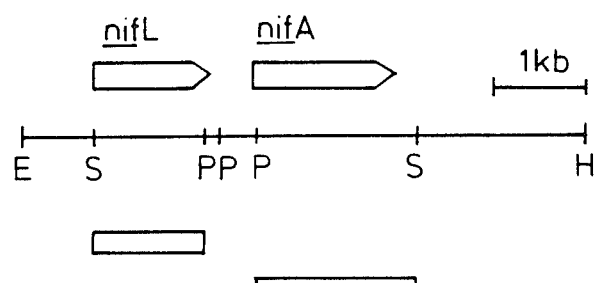

For both the nifH promoter and the fixA promoter of *R. meliloti*, it has been previously demonstrated that they can be activated in *E. coli* by the Klebsiella nifA gene product (Puhler, A. et al. (1983) supra). In the present study, the *E. coli* strains used in the isolation and identification of the *R. meliloti* fixD gene are listed (Table 1). Initially, plasmid pRmW54 was obtained by cloning a 3.5 kb HindIII fragment of pRm29D5 (Ruvkun, G. B. et al. (1982) Cell 29: 551–559) into the *E. coli* vector plasmid pAC177-C. This 3.5 kb HindIII fragment is the rightmost fragment on the restriction map presented in FIG. 1. pRm29D5 covers an 18 kb fragment adjacent to and surrounding the genes for nitrogenase (nif) and it was cloned from the genome of *R. meliloti*. The *K. pneumoniae* nifA probe (FIG. 2) was used in hybridization experiments to detect any complementary DNA fragment in pRmW54, pRmR3 and pRmW52. In FIG. 2, the coding regions of the *K. pneumoniae* nifA and nifL genes are shown in relation to the restriction map (Puhler, A. and W. Klipp (1981) In: Biology of inorganic nitrogen and sulfur; ed. Bothe, H. and A. Trebst; Berlin, Heidelberg). The two rectangles represent the restriction fragments which were used as radioactive DNA probes for the hybridization experiments with *R. meliloti* DNA carrying fix genes. The restriction endonucleases used were: E, EcoRI; S, SmaI; P, PstI and H, HindIII. Restriction fragments of the *R. meliloti* plasmids pRmW54, pRmR3 and pRmW52 were separated on agarose gels and blotted to nitrocellulose filters (FIG. 3a). This figure gives the results of Southern hybridization of *R. meliloti* fix DNA with the nifA and nifL specific DNA probes of *K. pneumoniae* following agarose gel electrophoresis of *R. meliloti* and *K. pneumoniae* restriction fragments. The results of various digestions are shown in the lanes of FIG. 3 as follows: Lane 1, an EcoRI-HindIII digest of the EcoRI-HindIII fragment (shown in FIG. 2) subcloned in pUC8 is given; Lane 2, λ-DNA digested with HindIII and EcoRI as molecular weight standards;

Lane 3, pRmW54 DNA digested with BamHI and BglII; Lane 4, pRmR3 DNA digested with HindIII and XhoI; and Lane 5, pRmW52 DNA digested with BamHI and XhoI. These filters were hybridized with radioactive labelled *K. pneumoniae* nifA fragments (FIG. 3b). This FIG. 3b illustrates an autoradiograph of nitrocellulose filters after hybridization with the *K. pneumoniae* nifA probe in 6×SSC at 55° C. Such conditions of hybridization are referred to herein as "stringent conditions". The 1.8 kb BamHI fragment and the adjacent 0.9 kb BamHI—BglII of pRmW54 are shown in Lane 3 (FIG. 3b) and they show homology to the *K. pneumoniae* nifA probe. The strong hybridization with other bands is due to vector-vector homology or to the *K. pneumoniae* control DNA shown in Lane 1. The hybridizing fragments are summarized in FIG. 4.

Figure 4:
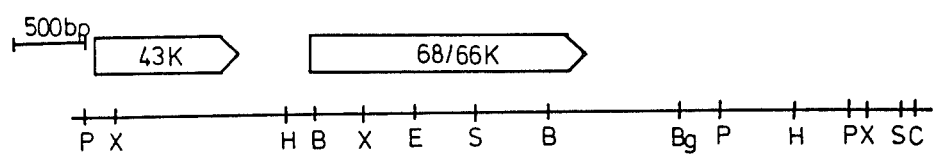

In addition (FIG. 3c) an autoradiograph of the various fragments transferred to nitrocellulose filters is shown when the *K. pneumoniae* nifL probe was used for hybridization in 6×SSC at 55° C. It can be seen that there is no specific hybridization to the nifL probe. The hybridizing *R. meliloti* gene region was covered by the 1.8 kb BamHI fragment, which contained the fixD gene (FIGS. 3 and 4). To a lesser extent, an adjacent 0.9 kb BamHI-BglII fragment was also hybridizing. It was found that this lesser hybridization was caused by the fact that the fixD gene extends over to a slight extent from the 1.8 kb BamHI fragment to the 0.9 kb BamHI-BglII fragment.

In FIG. 4, a restriction map of the *R. meliloti* fix gene region with fragments hybridizing to the nifA probe is shown. A black rectangle means strong hybridization, a hatched rectangle means weak hybridization and a white rectangle means no hybridization. This conclusion was confirmed by the nucleotide sequence of the coding region (FIG. 5) and by activation experiments (FIGS. 6 and 7).

FIG. 6 shows a restriction map of plasmid pGW6 (see Table 2) and also the results of a control experiment in which the *Rhizobium meliloti* nifH promoter was activated by the *Klebsiella pneumoniae* nifA gene product. The plasmid pGW6 contains an EcoRI-SmaI fragment of pRmR2 subcloned into pMC1403. The plasmid vector pMC1403 allows translational fusion to the eighth codon of the *E. coli* lacZ gene. β-galactosidase activity is detectable if a second plasmid constitutively expressing the *K. pneumoniae* nifA gene is present in the same cell. Plasmid pGW7 (Table 2) is a derivative of pGW6 where the reading frame of the fusion gene was corrected at the BamHI site by S1 nuclease digestion. In FIG. 7, the activation of the *Rhizobium meliloti* nifH promoter in pGW7 by the fixD gene product of *R. meliloti* is documented. The β-galactosidase activity of *E. coli* strain ET 8894 containing several plasmid combinations was measured. The results of six independent experiments are presented as black columns and the mean values are given as cross-lines. The plasmid combinations were: (1) pAc177-C+pGW7; (2) pRmW54+pGW7; (3) pRmW54::Tn5-1+pGW7; (4) pRmW54::Tn5-2+pGW7; (5) pRmW54::Tn5-5+pGW7; (6) pRmW54::Tn5-7+pGW7; (7) pRmW54::Tn5-8+pGW7; and (8) pRmW54::Tn5-9+pGW7. The plasmids are also shown schematically on the left side of the drawing. p stands for the aphI promoter (i.e., the kanamycin resistance gene) of the vector plasmid pAC177-C and the double line represents the *R. meliloti* HindIII restriction fragment of pRmW54. The triangles five the positions of the various Tn5 insertions and the black horizontal arrows show the fixD coding region. Note that the activation of the *R. meliloti* nifH promoter (compared to the control No. 1) was not detectable when Tn5 was in the fixD region. In addition it was shown that the nifL probe of *K. pneumoniae* did not hybridize to pRmW54, pRmR3 and pRmW52 (Table 2).

The fixD gene of *R. meliloti* was detected by expression of pRmW54 in *E. coli* minicells using methods already described in detail (Puhler, A. and W. Klipp (1981) In: Biology of inorganic nitrogen and sulfur; Bothe, H. and A. Trebst eds. Berlin, Heidelberg; and Weber, G. and A. Puhler (1982) Plant Mol. Biol. 1: 305–320). In *E. coli* minicells plasmid pRmW54 synthesized two polypeptides of 68K and 66K molecular weight (FIG. 8).

In FIG. 8, the restriction map of the HindIII fragment from pRmR29D5 (Table 2) is shown on the top and also the position of the several Tn5 insertions (arrows 1 through 9). Restriction enzymes used are denoted as follows: H, HindIII; B, BamHI; X, XhoI; E, EcoRI; Bg, BglII and P, PstI. The promoter of the aphI gene (kanamycin resistance gene of the vector plasmid pAC177-C) is indicated by p. The mapping shown in FIG. 8 is in good agreement with the fact that in minicells containing pRmW54::Tn5-1 to pRmW54::Tn5-4, the 68K/66K polypeptides were not detectable in SDS-acrylamide gels. In their place, lower molecular weight polypeptides were found indicating that in pRmW54::Tn5-1 to pRmW54::Tn5-4 the Tn5 insertions were within the coding region of the fixD gene. Using several Tn5 insertions in the cloned HindIII fragment the coding region, designated fixD was again localized to the 1.8 kb BamHI fragment (FIGS. 3 and 4). Especially, in the case of two Tn5 inserts (pRmW54::Tn5-2 and pRmW54::Tn5-4) putative truncated polypeptides were detected and this finding was in good agreement with the postulated coding region. Evidently, the 68K and 66K molecular weight polypeptides were both encoded by the same DNA fragment and may have been caused by the usage of different ATG-start codons. Both polypeptides are expressed on a very low level in *E. coli* minicells, but this low level is not due to a different codon usage in *R. meliloti* and *E. coli*, since the same coding region is very well expressed in the form of a fusion polypeptide with an *E. coli* vector gene, i.e., aminoglycoside phosphotransferase (aphI) (Example 6).

Thus, the experimental results disclosed in the present invention have defined the boundaries of the fixD gene of *R. meliloti* and have demonstrated that the protein of the fixD gene is responsible for the activation of the *R. meliloti* nifHDK and fixABC gene promoters leading in turn to the expression of the genes whose products are required for nitrogen fixation. However, the expression of the fixD gene requires that *R. meliloti* must first be in a symbiotic association with a specific host plant: *R. meliloti* does not fix nitrogen when living in a free state. Furthermore, *R. meliloti* does not fix nitrogen even when in a symbiotic association with the same host plant if there is a substantial quantity of nitrate already present in the soil. A genetic manipulation of the fixD gene so that it is consistently expressed either while free living or while in symbiotic association with a specific host plant growing in soil containing high nitrate would therefore be immensely useful in the fixation of nitrogen. Firstly the high nitrate content of a rich soil would not be decreased when an alfalfa-*R. meliloti* symbiotic association was present, but, to the contrary, the soil would become even richer in nitrates. In addition, the use of nif derepressed strains enables symbiotic nitrogen fixation to start earlier in nodule development and to last longer than in nodules with wild type Rhizobia.

Secondly, nif derepressed Rhizobium strains have a big advantage when a poor symbiotic association with other plant species leads to ineffective nodulation by wild type Rhizobia. A likely explanation of ineffective nodulation is that a special plant signal normally necessary for transcription of nif genes is absent. The nif derepressed strains described herein have the ability to fix nitrogen without such a plant signal.

Thirdly, Rhizobium strains can be induced to grow in close association with roots of economically important non-leguminous plants. Since the nif derepressed Rhizobium strains can fix nitrogen in large amounts while in the free living state, such an association between nif derepressed Rhizobia and the roots of important non-leguminous agricultural species has far reaching utility. The invention described here teaches how to make and use such nif derepressed Rhizobium strains.

The present invention discloses another useful application of the fixD promoter region. When R. meliloti exists in the free living condition, the promoter of the fixD gene remains inactive and it is only when a symbiotic relationship is established that the fixD gene is activated—most probably in direct or indirect response to a signal from the plant. It is often useful to incorporate a gene into a Rhizobium species but under such conditions that it is only expressed when the Rhizobia become symbiotically associated with the plant. This objective can be achieved in a genetic recombination by placing the coding region of a desirable gene under the control of the R. meliloti fixD gene promoter region. An example of such a gene, i.e., a gene whose expression is only desired when a symbiotic relationship has been established between a Rhizobium species and a plant, is the expression of the gene coding for an insecticidal protein such as the crystalline toxic protein of Bacillus thuringiensis (see Examples 3 and 4).

TABLE 1

| Strain | Escherichia coli strains | |
|---|---|---|
| | Reference | Remarks |
| E. coli DS410 | Dougan et al. (1977) | minicell isolation |
| E. coli MC1000 | Casabadan et al. (1980) | lacZ deletion strain |
| E. coli ET8894 | McNeil et al. (1981) | strain with a lacZ::IS1 insertion and glnALG deletion |

TABLE 2

| Plasmid | Plasmids | |
|---|---|---|
| | Reference | Remarks |
| pAC177-C | Puhler et al. (1983) | E. coli vector plasmid |
| pUC8 | Vieira and Messing (1982) | E. coli vector plasmid |
| pMC1403 | Casabadan et al. (1980) | E. coli for lacZ translational fusions |
| pRmR29D5 | Ruvkun et al. (1982) | R. meliloti nif/fix region; 25 kb ClaI |
| pRmR2 | Ruvkun et al. (1982) | R. meliloti nifHD; 3,9 kb EcoRI |
| pRmR3 | Ruvkun et al. (1982) | R. meliloti fix genes; 5 kb EcoRI |
| pWK131 | Puhler et al. (1983) | K. pneumoniae nifA cloned in pAC177-C |
| pWK130 | Puhler et al. (1983) | K. pneumoniae nifAL cloned in pAC177-C |
| pMM14 | Espin et al. (1982) | K. pneumoniae ntrC cloned in pACYC177 |
| pGW6/7 | G. Weber, Bielefeld | EcoRI-SmaI-subclone of pRmR2 into pMC1403 |
| pRmW54 | G. Weber, Bielefeld | HindIII-subclone of pRmR29D5 in pAC177-C |
| pRmW69 | G. Weber, Bielefeld | HindIII-XhoI-subclone of pRmW54 in pAC177-C |
| pRmW52 | G. Weber, Bielefeld | EcoRI-ClaI-subclone of pRmR29D5 in pBR325 |

TABLE 3

Activation of the R. meliloti nifH promotor in E. coli ET8894*

| Plasmids | gene products | β-galactosidase activity units per cell | |
|---|---|---|---|
| | | with ammonium | without ammonium |
| pGW7 pWK131 | K.p.nifA | 276,0 | 235,0 |
| pGW7 pWK130 | K.p.nifAL | 1,0 | 0,7 |
| pGW7 pMM14 | K.p.ntrC | 13,6 | 11,4 |
| pGW7 pRmW54 | 68K/66K | 1,4 | 1,4 |
| pGW7 pRmW54::Tn5 No 1 | | 0,8 | 0,8 |
| pGW7 pRmW54::Tn5 No 2 | | 0,8 | 0,9 |
| pGW7 pRmW54::Tn5 No 5 | | 0,6 | 0,7 |
| pGW7 pRmW54::Tn5 No 7 | 68K/66K | 2,6 | 2,3 |
| pGW7 pRmW54::Tn5 No 8 | 68K/66K | 3,2 | 2,2 |
| pGW7 pRmW54::Tn5 No 9 | 68K/66K | 3,4 | 4,1 |
| pGW7 pAC177-C | | 1,0 | 0,9 |

*The β-galactosidase activities of strains containing the indicated combinations of plasmids were measured in the presence or absence of ammonium in the medium (each number represents one measurement).

Example 1

Sequencing of the R. meliloti fixD gene

The two main techniques which exist for DNA sequence analysis are the chemical degradation method (Maxam, A. W. and W. Gilbert (1977) Proc. Nat. Acad. Sci. USA 74: 560–564) and the dideoxy-sequencing method (Sanger, F. et al. (1977) Proc. Nat. Acad. Sci. USA 74: 5463–5468). Both methods were used to determine the primary structure of the fixD gene of R. meliloti.

Figure 9:
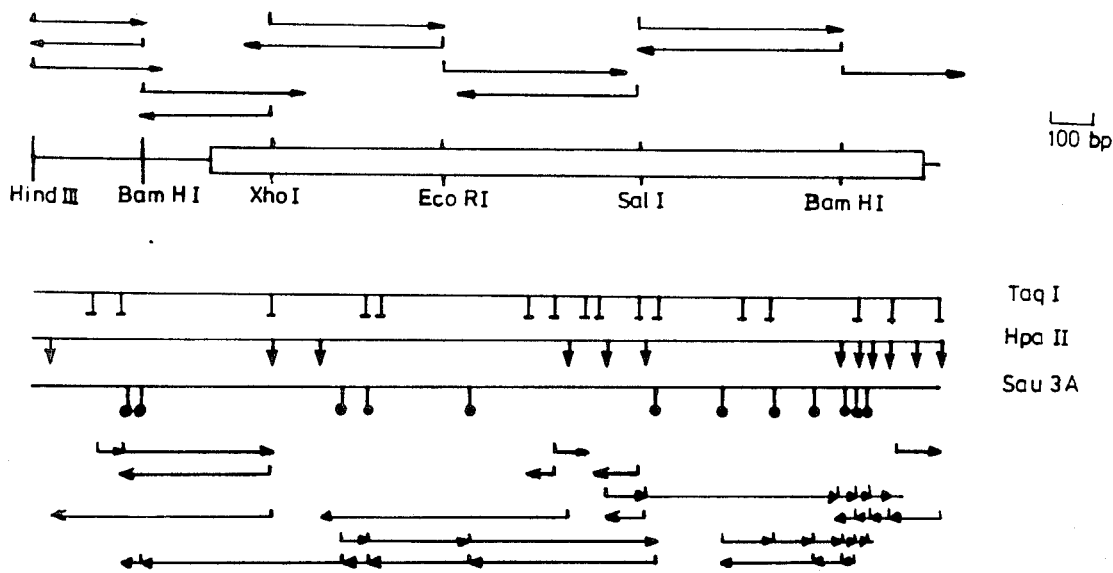
FIG. 9 presents the scheme used to sequence the *R. meliloti* fixD gene (Example 1). The map indicates M13 subclones and strategy.

The M13 cloning and sequencing vectors mp8, mp9, mp10 and mp11 (Messing, J. and Vieira, J. (1982) Gene 19: 269–276; Norrander, J. et al. (1983) Gene 26: 101–106) were used for subcloning of the HindIII 3.5 kb insert of plasmid pRmW54. For this purpose the HindIII fragment was cleaved from the vector by digestion with HindIII and then separated and isolated by agarose gel electrophoresis. For a non-random sequencing approach, the DNA was cleaved with various restriction enzymes (EcoRI, BamHI, HindIII, SalI, XhoI) and subcloned into the appropriate restriction sites of the M13 sequencing vectors. "Shotgun" cloning was carried out by digestion of the HindIII fragment with the restriction endonucleases Sau3A, HpaII and TaqI. The resulting fragments were again cloned into M13 sequencing vectors. Recombinant clones were sequenced by the method of Sanger but slightly modified (Messing, J. et al. (1981) Nucleic Acids Res. 9: 309–321). The strategy for dideoxy sequencing is presented (FIG. 9).

To implement the sequencing strategy, subclones of a DNA fragment containing the fixD coding region were generated and sequenced by a non-random and "shotgun" approach. In FIG. 9, the position and extension of the subclones are presented in relation to the final restriction map of the fragment. The arrows (FIG. 9) indicate the direction of sequencing and the rectangle represents the only open reading frame of the analysed DNA fragment.

Figure 11:
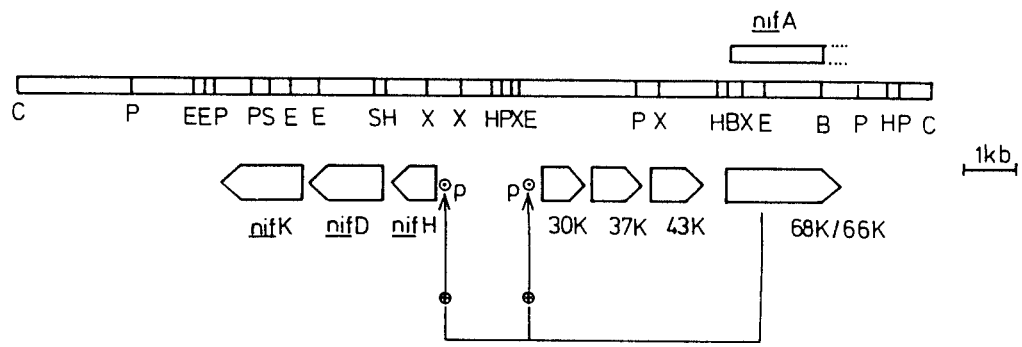

Restriction mapping of the HindIII fragment revealed the presence of several convenient restriction sites suitable for sequencing by the chemical method (Maxam, A. M. and W. Gilbert (1977) supra) (FIG. 9). The HindIII fragment was isolated as described (supra), digested with the restriction enzymes EcoRI, BamHI, SalI and XhoI and subcloned into a pUC8 sequencing vector (Vieira, J. and J. Messing (1982) Gene 13: 259–268). Determination of the sequence around several restriction sites of the fragment (FIG. 9) enabled further alignment and confirmation of the data obtained from the dideoxy sequencing. The combined results of the two sequencing methods yielded the sequence of 2127 bp of the 3.5 kb HindIII fragment (FIG. 10). Inspection of the six possible reading frames of the nucleotide sequence revealed that only one frame was large enough to code the fixD polypeptide. All other reading frames were closed by termination codons at many places. The large open reading frame which represents the fixD gene of R. meliloti started with an ATG 415 nucleotides from the HindIII site and spanned 1638 nucleotides. The coding region of fixD determined by the minicell procedure contained the following series of restriction sites: XhoI, EcoRI and BamHI. The same series of restriction sites was also present in the open reading frame. In addition, the molecular weight determination of the polypeptide encoded by the open reading frame resulted in a value of 59K, comparable to the imprecise molecular weight determination of 66/68K determined by the minicell procedure. An overall map of the fix genes and the nif genes is shown (FIG. 11)

The hypothesis that the polypeptide double band of 66/68K detected in the minicell procedure is caused by different ATG start codons is supported by the nucleotide sequence. In addition to the ATG start codon at nucleotide 415, further ATG codons are located at positions 469 and 535.

Example 2

Activation of the Rhizobium meliloti nifH promoter by the R. meliloti fixD gene products in Escherichia coli Following the hybridization experiments which localized the fixD gene on pRmW54, it was demonstrated that the R. meliloti fixD gene products activated the R. meliloti nifH promoter in E. coli. For these experiments plasmid pGW6, which contains the R. meliloti nifD gene fused on a translational level to a plasmid borne lacZ gene, was constructed (FIG. 6). Control experiments with plasmid pWK131 (Table 2) which constitutively expressed the K. pneumoniae nifA gene showed that the nifD-lacZ fusion of pGW6 was activated. The activation was detected by measuring the $\beta$-galactosidase activity (FIG. 6). In spite of the differences in activation of the R. meliloti nifH gene and the K. pneumoniae nifH gene by the glnG gene of E. coli, it was possible that the R. meliloti fixD gene product might activate the R. meliloti nifH promoter and be detectable in the same manner. For the actual experiment, an E. coli strain ET8894 (Table 1) which carries an IS1 insertion in the chromosomal lacZ gene and a deletion in the gln regulatory region, was used. This train was transformed with plasmid pGW7 and plasmid pRmW54. The results (FIG. 7) were as follows: ET8894 containing the nifD::lacZ fusion (pGW7) and the constitutively expressed fixD gene (pRmW54) had a 1.5-fold higher $\beta$-galactosidase activity compared to the control strain ET8894 containing the plasmid pAC177-C (Table 2; FIG. 7). The significance of this activation on a very low level was shown by the use of Tn5 insertions in the cloned fixD gene. Only Tn5 insertions in the coding region resulted in the abolishment of the activation (Table 2; FIG. 7).

Example 3

Expression of foreign genes under the control of a fixD promoter DNA region.

Figures 12, 13, 14:
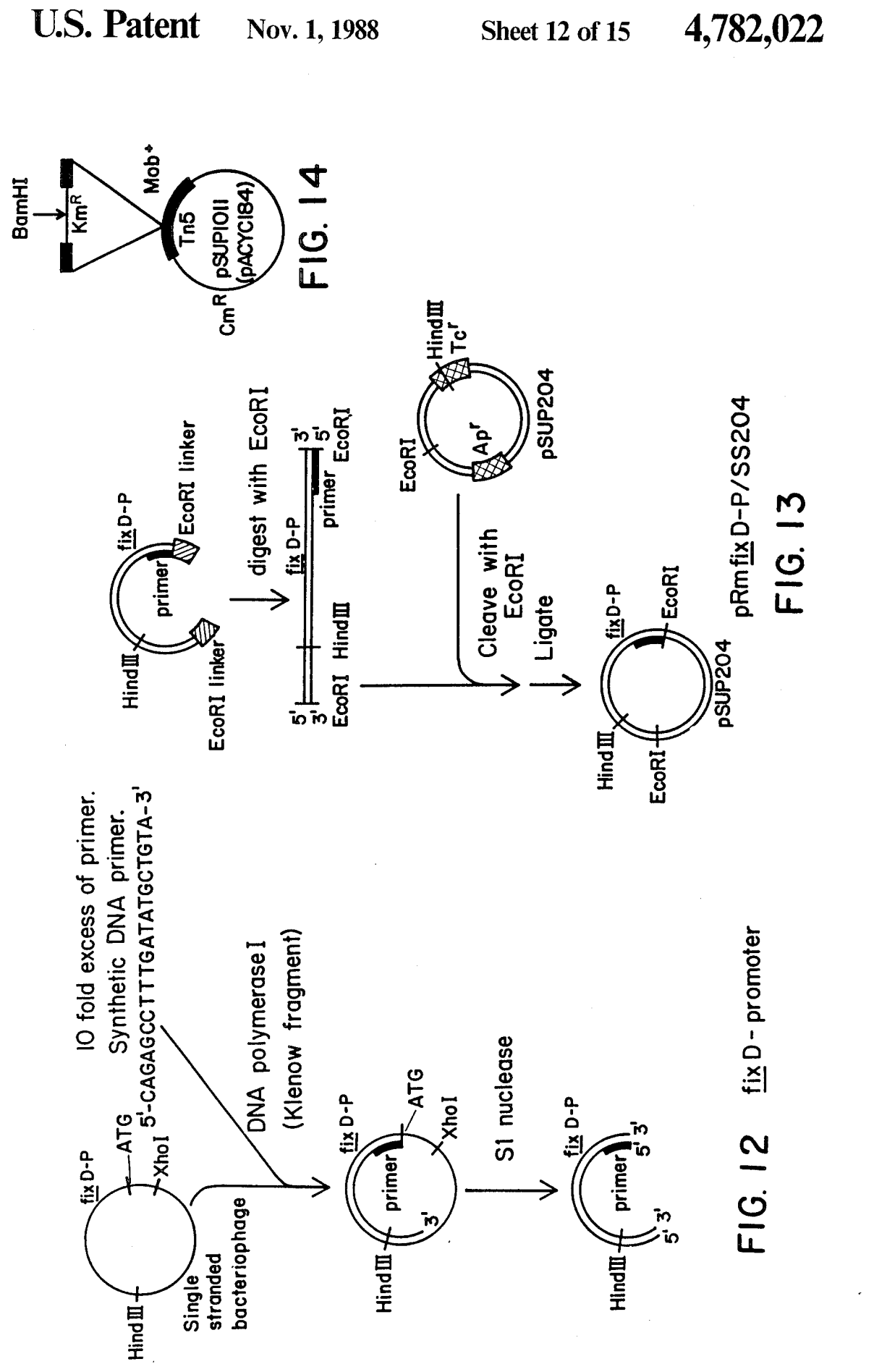

Construct a synthetic DNA primer which is complementary to the DNA sequence immediately upstream (i.e., 5'-to the ATG translation initiation codon) of the Rhizobium meliloti fixD coding sequence. The synthetic DNA primer has the sequence 5'-CAGAGCCTTT-GATATGCTGTA-3'. The HindIII-XhoI DNA subclone of pRmW54 in pAC177-C (designated pRmW69—Table 2) is then excised, purified, subcloned into a single stranded DNA phage and transformed into E. coli JM103 (FIG. 11). This HindIII-XhoI subclone contains the complete promoter sequence of R. meliloti fixD gene and 82 nucleotides at the 5'-end of the fixD coding sequence. The subcloned fragment is amplified therein and single stranded templates (ca. 1 $\mu$g) are recovered from the supernatant following centrifugation of the bacterial host. A 10-fold excess of the synthetic DNA primer in the presence of the four deoxynucleotide triphosphates (one of which is radioactive) and DNA polymerase I (Klenow fragment) is now used as a primer on this fixD template to generate double stranded DNA (dsDNA) (FIG. 12). The mixture is incubated for a period (e.g., 15–45 minutes) at an appropriate temperature (e.g., 25°–37° C.) during which period the complementary strand is extended beyond the HindIII site. The 468 nucleotide region between the HindIII site and the ARG initiation codon contains the complete promoter region of the fixD gene of R. meliloti. The remaining single stranded DNA is then removed by digestion with S1 nuclease (FIG. 12). EcoRI linkers (GGAATTCC) are then ligated to the dsDNA fragments followed by digestion with EcoRI (FIG. 13). The fragments are separated by agarose gel electrophoresis and the fragment containing the promoter sequence is eluted and cloned into the wide host range plasmid pSUP204 (FIG. 13), which has previously been restricted by the restriction enzyme EcoRI. The resulting recombinant plasmid is termed pRm-fixD-P/SS204. Following transformation and amplification in a suitable *E. coli* host strain, e.g., 17-1, which is restriction negative, i.e., r⁻, partial cleavage with EcoRI allows the addition of any foreign structural gene or foreign DNA fragment into the linearized plasmid downstream from the fixD promoter fragment. A foreign structural gene of foreign DNA fragment is herein defined as any structural gene or DNA fragment not found naturally under the direct or indirect control of a fixD promoter. For example, the gene coding for the crystalline toxic protein of *Bacillus thuringiensis* can be inserted resulting in a "composite" recombinant. A composite recombinant is herein defined as a recombinant DNA plasmid containing a vector, a promoter sequence and any foreign DNA whose expression is under the control of said promoter sequence.

Example 4

Insertion of the bacterial toxin gene from *Bacillus thuringiensis* into the recombinant plasmid pRmfixD-P/SS204

Recombinant plasmids containing inserts of the gene encoding the toxic crystal protein of *B. thuringiensis* are obtained using the techniques described (Wong, H. C., Schnepf, H. E. and H. R. Whiteley (1983) J. Biol. Chem. 258: 1960–1967). The recombinant plasmid pES1 (ATCC Number 31995) consisting of the plasmid vector pBR322 and DNA homologous to the 30, 32 and 37 megadalton plasmids, as well as DNA homologous to linearized forms of the very large plasmids of *B. thuringiensis* is partially cleaved with EcoRI to give linear molecules. These partial cleavage products are further restricted by the enzyme AvaI. The digestion conditions are as recommended by the manufacturer. A probe for the toxic crystal protein gene is isolated and radioactively labelled as previously described (Wong, H. C. et al. (1983) supra). The restriction fragments are separated by agarose gel electrophoresis and the labelled probe is found to hybridize to one fragment of approximately 15 kilobases (kb). This fragment includes the EcoRI fragments D and F (Wong, H. C. et al. (1983) supra). The 15 kb fragment is then cloned into M13mp8 or M13mp9 according to standard procedure (Messing, J. and J. Vieira (1982) Gene 19: 269–276) and transformed into *E. coli* JM103. The single stranded DNA from the extruded phage particles is purified and replicated in vitro by use of a synthetic primer (5'-TGTTATCCATGGGTTACCTCC-3') (The general method of site specific mutagenesis is described in Zoller, M. J. and M. Smith (1982) Nucleic Acids Research 10: 6487–6500). The resulting double stranded recombinant plasmid is then transformed back into *E. coli* JM103 and amplified. The amplified double stranded recombinant DNA is purified from the *E. coli* JM103 cells and cleaved with the restriction endonucleases NcoI and AvaI. NcoI cleaves at the site of the synthetic primer (which is the initiation site of the toxic crystal protein gene) and AvaI cleaves at a site which is downstream from the 3'-end of the toxic crystal protein gene. The overhangs are then filled in to blunt ends (Maniatis, T., Jeffrey, A. and D. G. Kleid (1975) Proc. Nat. Acad. Sci. U.S.A. 72: 1184–1188).

Finally the pRmfixD-P/SS204 recombinant plasmid which is derived from pSUP204 (FIG. 13) is cleaved with EcoRI and the overhangs filled in to blunt ends. HindIII linkers are then added to both the *B. thuringiensis* toxic crystal protein gene fragment and to the pRmfixD-P/SS204 recombinant. Following the HindIII digestion of both components, the toxic crystal protein gene and the pRmfixD-P/SS204 recombinant plasmid are ligated together to give a pRmfixD-P/SS204—*B. thuringiensis* toxic crystal protein gene composite. The mixture is transformed into a suitable *E. coli* host, e.g. K802, 17-1 or RR1. Plasmids are isolated from individual colonies and the orientation determined by restriction mapping. A colony containing a plasmid with the correct orientation is then conjugated to *Rhizobium meliloti* and the plasmid is transferred as already described (Example 7). The production of mRNA and/or the toxic crystal protein is monitored as already described (Wong, et al., supra).

Example 5

Construction of a recombinant plasmid containing the fixD gene of *R. meliloti* under control of a constitutive kanamycin resistance gene promoter The source of the kanamycin resistance gene is the transposon Tn5 and the suicide vector pSUP1011 (Simon, R., Priefer, U. and A. Puhler (1981) Proc. of Bielefeld Symposium, Springer-Verlag, West Germany) (see FIG. 14). Transposon Tn5 is a DNA element of 5.7 kilobases (kb) in length, consisting of 1.5 kb inverted repeat sequences flanking a 2.7 kb central region. Encoded within the inverted repeats are the functions required for transposition. The central region of the transposon carries a gene conferring resistance to the antibiotic kanamycin (Km$^r$). The coding region of the neomycin phosphotransferase gene (neo) (alternatively named aminoglycoside phosphotransferase gene-aph) is deleted by digestion with the restriction enzymes BglII (a BglII site is present 36 nucleotides upstream from the translational start codon ATG) and SalI (a SalI site is present 342 nucleotides downstream from the TGA termination codon) (see FIG. 15).

Figures 16, 17:
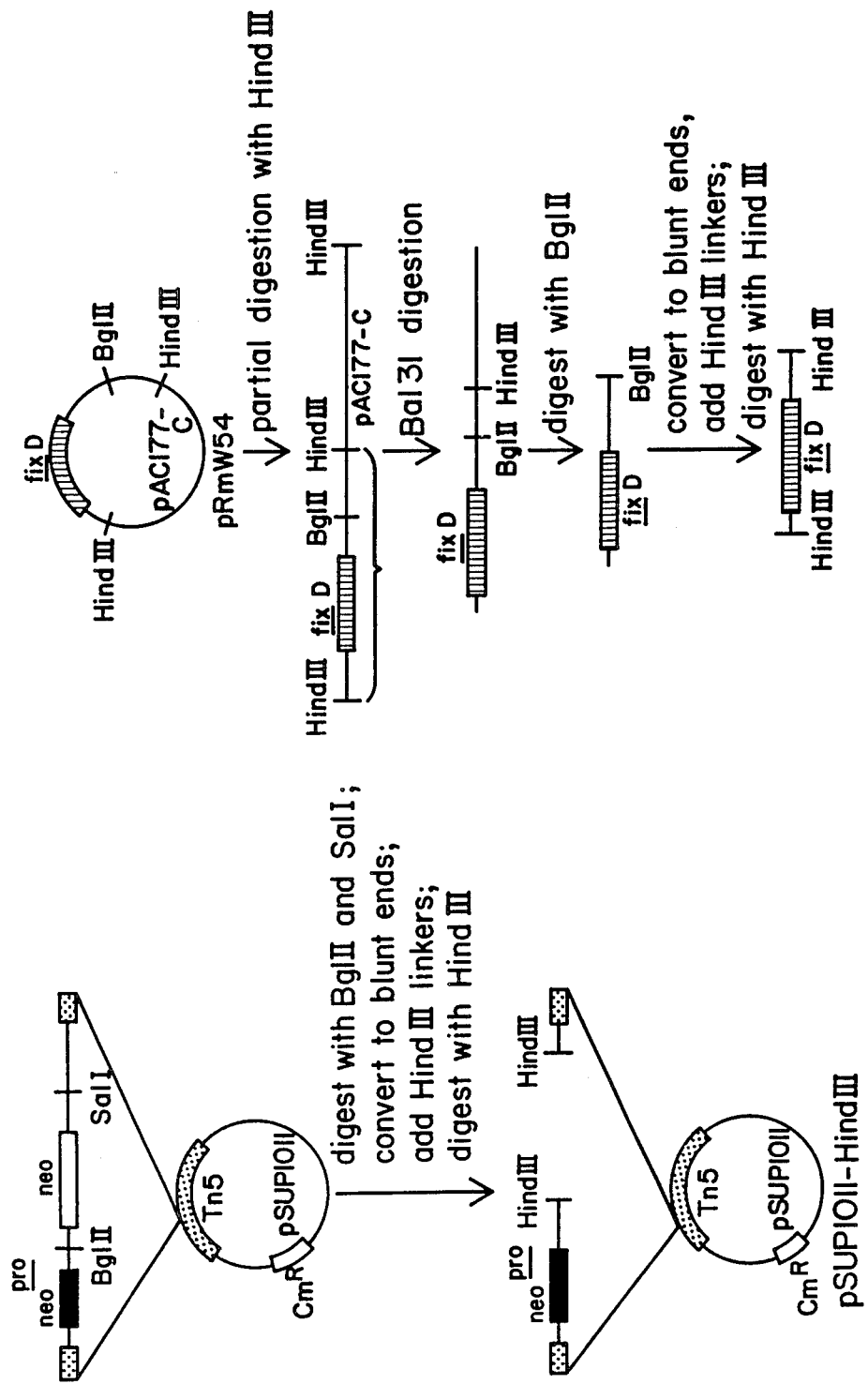
FIG. 16 diagrams construction of plasmid having a convenient HindIII site suitable for structural gene insertion behind a kan promoter (Example 5).
FIG. 17 diagrams preparation of a fixD structural gene suitable for placement behind the kan gene promoter (Example 5).

The sequence of the kanamycin resistance gene has been previously shown and is reproduced herein as FIG. 15 (Beck, E. et al. (1982) Gene 19: 327–336). The nucleotide sequence of Tn5 DNA from position 1401 to position 2700 is shown. The aph coding region is boxed by solid lines. Some restriction sites are indicated in the sequence, as well as at the end of the left inverted repeat (closing bracket, [ ) and the promoter region. Such a deletion leaves the promoter region of the neomycin phosphotransferase gene (neo) intact. The single stranded overlaps generated by these two restriction endonucleases are converted to blunt ends and HindIII linkers are added, followed by digestion with HindIII restriction endonuclease. This construction is herein defined as pSUP1011-HindIII (FIG. 16).

Figures 18, 19:
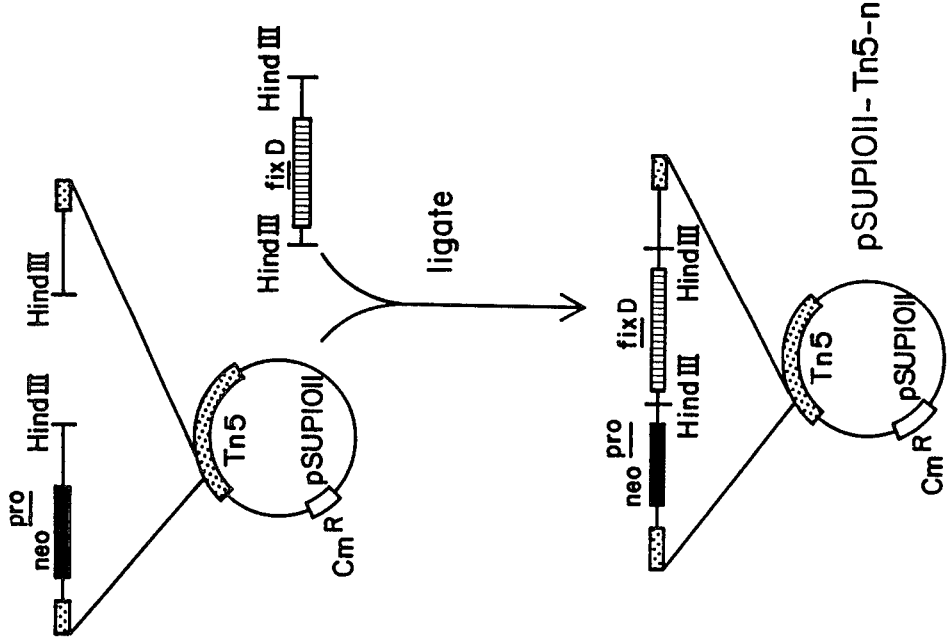
FIG. 18 diagrams combination of a kan gene promoter with a fixD structural gene to form pSUP10-11—Tn5-neo$^{pro}$fixD (Example 5).

In parallel, plasmid pRmW54 was obtained by cloning a 3.5 kb HindIII fragment of pRm29D5 (Ruvkun, G. B. et al. (1982) Cell 29: 551–559) into the *E. coli* vector plasmid pAC177-C (Table 2). After transformation into a suitable host strain and amplification, the recombinant plasmid is linearized by partial digestion with the restriction endonuclease HindIII. Linearization occurs either on the upstream side of the fixD gene or on the downstream side. These two alternatives can be distinguished by the use of restriction maps. Those linearizations where the cut occurs upstream (i.e., 5' to the reading strand of the fixD gene) are retained and treated with the exonuclease BAL31 for a sufficient period to produce a blunt end at an optimal distance from the ATG initiation codon of the *R. meliloti* fixD gene. The linearized recombinant which is thus shortened towards the 5'-terminus of the fixD gene is then further restricted with BglII. A single BglII site is present downstream (i.e., 3'—from the TGA termination codon of the reading strand) from the termination codon of the fixD gene (FIG. 17). This fragment which contains the fixD structural gene is converted to blunt ends and HindIII linkers are added. Following digestion with HindIII, the fragment containing the fixD gene is purified and ligated into the linearized pSUP1011-HindIII (supra) (FIG. 18). Such a construction comprises the pSUP1011 suicide vector and a Tn5 transposon. Between the inverted repeats of the Tn5, the neomycin phosphotransferase promoter (neo$^{pro}$) is included and, in addition, the fixD structural gene positioned so that it is under the control of neo$^{pro}$. This construction is herein defined as pSUP1011-Tn5-neo$^{pro}$-fixD.

Example 6

Construction of a fusion gene and product protein of fixD and aminoglycoside phosphotransferase In order to obtain such a fusion gene and protein product, the XhoI-HindIII subfragment of pRmW54 was cloned into pAC177-C (Table 2). From the restriction mapping experiment (Example 1) it was known that the XhoI site was located within the fixD coding region. On the other hand, the XhoI restriction site of the vector plasmid pAC177-C was located in the aphI gene (kanamycin resistance gene). In order to obtain the correct reading frame of the fusion polypeptide, the XhoI site was treated with S1 nuclease in one case and with DNA polymerase I in the other. A strongly expressed 60K fusion polypeptide was obtained after treatment with DNA polymerase I. The recombinant plasmid described herein which contains such a constitutively expressed fixD gene is referred to as pRmW69 (Table 2).

Example 7

Introduction of DNA sequences into the genome of gram-negative organisms other than E. coli This example is based on the following general principles. Two basic components are employed. These are: (1) a suicide vector and (2) a transposon.

Suicide vectors are plasmid molecules which replicate stably in one bacterial host (in this case E. coli) but fail to replicate in a different bacterial species (e.g., Rhizobium meliloti).

Transposons are genetic elements which are able to move (translocate) from one location to another in DNA. The translocation process is mediated by gene products encoded on the transposon and is dependent on the integrity of repeated sequences (directly or indirectly repeated) located at each end of the transposon. Transposons generally carry a gene (or genes) encoding resistance to one or more antibiotics.

The vector contains the inserted fixD gene under the control of a kanamycin resistance promoter pSUP1011-Tn5-neo$^{pro}$-fixD (see Example 5) and is transformed (introduced) into Escherichia coli strain SM10. This type of recombinant plasmid comprising a suicide vector, a transposon and a constitutively expressed structural gene is herein defined as a "constitutive gene transfer system". (This strain is capable of mobilizing (Mob+) pSUP1011 derivatives (recombinant plasmids) into other gram negative bacteria) (Simon, R., Priefer, U. and A. Puhler (1983) Proc. of Bielefeld Symposium, Springer-Verlag, West Germany). The resultant transformants are screened by the Grunstein and Hogness colony hybridization procedure (Grunstein, M. and D. S. Hogness (1975) Proc. Nat. Acad. Sci. USA 72: 3961ff) to detect those containing the desired cloned DNA fragment.

Introduction of the cloned DNA fragment into the genome of any gram-negative bacterium (e.g., Rhizobium meliloti) is achieved via a process called bacterial conjugation. The E. coli SM10 derivative, carrying the desired pSUP1011 recombinant, is mixed with cells of R. meliloti carrying a symbiotic (Sym) plasmid on the surface of a nutrient agar plate. The plate is incubated for a suitable period (4–16 hours) at 29°–30° (optimum temperature for Rhizobium meliloti) and during this time cells of each type come into physical contact (conjugation) and the pSUP1011 recombinant derivative is transferred from E. coli to R. meliloti. The cell mixture is washed off the plate and spread on an agar plate which is selective for organisms which can only grow if they are capable of constitutive nitrogen fixation. The resultant colonies which can constitutively fix nitrogen will be derivatives of R. meliloti in which the cloned DNA fragment, within Tn5, will be inserted at some point in the genome. Selection for ability to constitutively fix nitrogen insures maintenance of the inserted DNA.

At this stage, it is unknown whether the DNA fragment, within Tn5, has been transferred to the chromosome of R. meliloti or to one of its several plasmids. This uncertainty can be resolved by visualization of the plasmids and the bacterial chromosome by ethidium bromide staining after horizontal agarose gel electrophoresis (Djordjevic, M. A. et al. (1982) J. Bacteriol. 151: 560-568). In either case, the transferred DNA fragment is fuctional, since the fixD gene product acts in trans to activate nitrogen fixation.

E. coli C600 (pRmW54) was placed on deposit with the American Type Culture Collection, 12301 Parklawn Drive, Rockville, MD 20852 on June 4, 1984, Accession No. 39722.

Example 8

Enhanced Expression of Foreign Gene Under nif Promoter Control Resulting from Enhanced Expression of fixD Gene Products Expression of β-galactosidase was placed under nifHDK promoter control as described (pGW7, Example 2, FIG. 6). The amount of β-galactosidase synthesized under nifHDK control was measured using E. coli ET8894 (Table 1) containing pGW7. Synthesis of active β-galactosidase in this system depends on activation of the nifHDK promoter. Introduction of pRmW54 (expressing fixD as a fusion protein under control of the aphI) leads to a significant increase in β-galactosidase activity over control levels (Table 3). The described experiment was designed to test whether β-galactosidase expression could be enhanced by increasing the levels of fixD gene product, and whether the level of fixD gene product could be increased by shortening the distance, or number of amino acids, between the aphI promoter and the start of the fixD gene.

A series of deletions was constructed in which the number of amino acids lying in the coding region between the aphI promoter and the fixD coding region was reduced. First, the larger of the two HindIII-BglII fragments of pRmW54 was cloned into pACYC177-C (also termed pAC177-C herein), previously cut with HindIII and BamHI. The resulting plasmid, designated pRmW541, contained a unique HindIII site located between the aphI promoter and the fixD coding region. Deletions were introduced by cutting pRmW541 with HindIII and digesting for various times with exonuclease Bal31. The resulting digestion mixture was religated after S1 nuclease digestion, and the mixture was used to transform a culture of *E. coli* ET8894 (pGW7). After incubation for 48 hours at 30° C., the transformants were plated on agar plates supplemented with ampicillin, chloramphenicol, glutamine and X-gal (5-bromo-4-chloro-3-indolyl-β-D galactoside, a chromogenic β-galactosidase substrate). Although *E. coli* ET8894 (pGW7, pRmW54) produces detectable β-galactosidase activity, the activity is low and incubation on X-gal plates yields white colonies. Several transformants from the deletion mixture yielded blue colonies, indicating qualitatively enhanced expression of β-galactosidase. Plasmids were isolated from strains with higher activity and retransformed into *E. coli* ET8894 (pGW7). The β-galactosidase activity was quantitatively measured with results shown in FIG. 19. The structure of each of each of the pRmW541 deletion plasmids was further analyzed by sequencing XhoI fragments of the various pRmW541 isolates. An endonuclease XhoI site exists within the fixD gene and another is located just upstream from the translation start of the aphI coding region (See FIG. 10). The XhoI fragments were se- The effect of the deletions on the expression of the FIX-D polypeptides was also measured. Deletions in plasmid pRmW541 which cause a high level of activation of the nifHDK promoter also lead to stronger expression of the FIX-D polypeptide.

The results demonstrate that deletions in the region between the aphI promoter and the fixD gene made it possible to increase the level of APH-I-FIX-D fusion protein synthesized and to increase the activation of the nifHDK-lacZ fusion. Control experiments have shown that activation on the nifHDK promoter by the fixD gene product was strictly dependent on the presence of an intact glnF gene in the host organism. The glnF gene, also termed ntrA, is a positive regulatory gene for glutamine synthetase, and is active in ET8894.

What is claimed is:

1. A recombinant DNA molecule capable of functioning as a vector comprising,
   (a) a promoter of a *Rhizobium meliloti* fixD gene, and
   (b) a foreign structural gene under control of said promoter.
2. A recombinant DNA as recited in claim 1 wherein said vector functions are derived from pSUP204.
3. A recombinant DNA plasmid as recited in claim 1 wherein said promoter comprises the nucleotide sequence

```
5'-A—A—G—C—T—T—A—A—A—C—C—T—G—C—C—T—C—G—C—G—C—T—C—A—C—G—C—G—A—G—
T—C—T—T—G—C—C—C—G—G—C—C—A—A—A—A—G—T—T—G—A—A—T—G—A—A—A—
C—T—G—G—C—A—A—G—T—G—G—A—A—G—T—C—A—C—T—G—C—C—G—A—T—G—G—C—T—G—C—A—T—
G—G—A—G—T—G—C—G—G—C—A—C—A—T—G—C—A—G—A—G—T—G—T—T—G—T—G—C—G—A—G—G—C—A—
A—A—C—G—G—T—G—A—C—G—T—C—G—A—G—T—G—G—A—G—C—T—A—T—C—C—A—C—G—A—G—G—T—G—
G—C—T—T—C—G—G—T—G—T—C—C—T—T—C—A—A—G—T—C—G—G—A—T—G—A—G—C—C—A—C—
T—C—T—A—A—G—T—C—G—A—T—T—C—A—C—A—A—G—C—T—A—G—A—T—C—G—G—C—G—T—T—C—A—
A—T—A—G—G—G—G—A—C—G—A—A—G—T—G—C—C—A—G—G—G—A—T—C—C—T—T—A—C—A—A—G—A—
A—C—C—A—A—C—T—T—A—C—C—T—T—C—C—G—T—A—A—C—T—T—T—A—T—C—G—C—T—C—T—C—C—G—
A—C—T—G—T—C—A—A—T—A—C—G—C—A—T—A—C—C—T—C—C—T—A—A—T—A—T—T—A—A—A—G—C—G—G—
G—C—G—A—G—A—A—A—A—T—G—A—C—T—A—A—G—G—T—G—C—T—C—C—C—A—T—C—G—C—A—A—C—T—
C—G—T—T—C—A—G—G—G—G—A—G—T—T—A—G—T—G—C—C—C—T—G—T—C—T—G—T—A—C—C—T—T—C—
A—C—A—A—A—G—A—G—A—C—A—T—G—C—G—C—A—A—A—C—A—G—G—A—C—A—A—G—C—G—C—T—C—C—
G—C—C—G—A—A—A—T—T—T—A—C—A—G—C—A—T—A—T—C—A—A—A—G—G—C—T—C—T—G—3'
``` quenced, after cloning them into the SalI site of the phage M13mp8. Nucleotide sequence determination of these deletions, which were contained within the XhoI fragments, revealed that all the nifHDK activated proteins were fusion polypeptides, with the exception of pRmW541-5. The structures are shown diagrammatically in FIG. 19.

FIG. 19 diagrams the structure of the pRmW541 deletion plasmids, and the resulting level of activation in ET8894 (pGW7). For each of the plasmids the concluded polypeptide structure is shown schematically. The black closed circle indicates the aphI promoter. The open rectangles represent the APH-I part of the translated polypeptide. The incomplete black triangle represents the FIX-D part. Crosshatched regions indicated translated open reading frame regions generated by the construction, which are expressed only in the fusion polypeptides. The numbers in the boxes represent the amino acid residues. The plated right-hand end of the hatched region of pRmW541-5 indicates a translation terminal signal. The numbers on top of the FIX-D part indicate the codon in which the fusion occurred. The right-hand column shows the β-galactosidase activity of each plasmid in ET8894 (pGW7).

or a functionally equivalent sequence hybridizable thereto under stringent conditions.

4. A recombinant DNA plasmid as recited in claim 1 wherein said foreign structural gene is a bacterial toxin gene of *Bacillus thuringiensis*.
5. A recombinant DNA molecule capable of functioning as a vector comprising
   (a) a promoter of a constitutively expressed gene, and
   (b) a coding sequence of a fixD gene of a Rhizobium species which codes for a product capable of activating *R. meliloti* nifHDK and fixABC promoters, under control of said promoter.
6. A recombinant DNA as recited in claim 5 wherein said vector functions are derived from a suicide vector.
7. A recombinant DNA as recited in claim 6 wherein said suicide vector comprises pSUP1011 and said recombinant DNA comprises a transposon Tn5.
8. A recombinant DNA plasmid as recited in claim 5 wherein said promoter is a promoter of a kanamycin resistance gene.
9. A recombinant DNA plasmid as recited in claim 5 wherein said promoter of said kanamycin resistance gene comprises the nucleotide sequence

```
5'-A—C—A—G—C—A—A—G—C—G—A—A—C—C—G—G—A—A—T—T—G—C—C—A—G—C—T—G—G—G—G—C—G—
C—C—C—T—C—T—G—G—T—A—A—G—G—T—T—G—G—G—A—A—G—C—C—C—T—G—C—A—A—A—G—T—A—A—
```

A—C—T—G—G—A—T—G—G—C—T—T—T—C—T—T—G—C—C—G—C—C—A—A—G—G—A—T—C—T—G—A—T—G—
G—C—G—C—A—G—G—G—A—T—C—A—A—3' or a functionally equivalent sequence hybridizable thereto under stringent conditions.

10. A recombinant DNA plasmid as recited in claim 5 wherein said fixD gene comprises the nucleotide sequence 5'-A—T—G—G—C—C—C—C—A—C—T—C—G—T—C—T—T—G—A—G—A—C—C—A—C—G—C—T—A—A—C—A—
A—T—T—T—C—G—T—G—A—A—T—A—C—C—C—T—C—T—T—T—G—A—T—T—C—T—G—C—G—C—A—T—
G—C—G—C—C—G—G—C—G—G—A—C—T—C—G—A—G—A—T—T—C—C—G—C—G—T—C—G—A—A—
G—G—A—G—A—G—A—C—A—A—G—A—T—A—C—A—G—C—G—G—C—T—A—C—C—C—G—C—A—A—C—A—
G—C—G—G—G—T—C—T—C—C—T—T—C—T—G—C—C—G—C—T—G—A—T—T—A—T—A—C—T—G—T—A—C—C—A—
A—A—G—G—C—C—G—C—A—A—T—A—G—A—C—A—A—G—T—C—A—T—G—A—C—T—G—C—C—G—G—C—
G—G—C—T—G—G—T—C—G—T—A—C—C—A—A—G—A—C—G—T—T—T—G—C—A—A—C—T—C—T—G—A—G—C—T—
G—T—T—C—A—A—G—G—A—T—C—A—G—A—T—A—A—A—A—T—G—G—C—G—C—G—G—A—A—T—G—G—T—
C—C—G—A—C—T—G—C—C—T—T—C—A—T—C—G—C—T—G—C—G—G—C—G—G—T—G—G—A—G—G—T—C—G—
A—T—C—A—A—C—G—A—A—A—A—C—G—G—C—G—G—A—A—T—G—C—T—G—T—G—G—T—T—C—G—A—G—T—G—
C—G—C—C—G—A—A—A—G—A—G—T—C—C—G—G—A—A—T—T—A—T—G—A—G—G—A—G—A—G—
G—T—A—C—A—C—T—T—T—C—T—T—T—C—T—A—T—G—G—C—C—G—C—C—A—A—T—C—T—T—G—C—G—G—
G—G—A—G—G—G—C—C—A—T—T—C—G—G—C—T—T—C—A—T—C—G—C—A—C—A—A—T—C—A—G—C—A—G—
G—C—G—T—C—A—G—C—G—G—A—C—A—A—T—T—T—G—C—C—G—A—A—G—A—G—C—A—G—C—A—A—G—A—A—
C—A—A—A—C—G—A—A—T—T—C—A—C—G—T—G—A—G—C—A—G—A—C—A—G—C—A—G—A—G—T—T—
C—C—G—C—C—C—G—C—C—A—G—C—G—G—C—T—G—C—T—C—A—A—G—A—A—T—G—A—C—G—G—A—T—
C—A—T—C—G—G—G—G—A—A—A—G—T—A—C—C—G—C—C—T—C—A—T—G—A—C—G—G—C—G—G—T—A—
G—A—T—A—C—C—G—C—C—A—A—A—G—T—C—A—T—G—G—C—A—G—A—G—A—C—A—A—T—T—C—A—A—
T—C—G—T—T—C—T—C—C—T—T—A—G—G—G—G—A—A—C—A—G—A—A—C—T—G—G—C—A—A—
G—G—A—A—T—G—C—T—T—T—C—C—G—A—A—G—C—T—A—A—T—C—C—A—C—A—C—G—C—A—T—C—G—
A—C—T—C—G—G—C—A—A—A—A—A—A—A—G—C—C—C—T—T—C—A—T—C—A—A—G—T—T—C—A—A—T—T—
G—C—C—C—G—C—G—C—T—G—T—C—T—G—A—G—A—G—C—C—T—T—C—T—C—G—A—A—T—C—A—G—A—
G—C—T—G—T—T—T—G—G—A—C—A—T—G—A—A—A—G—G—T—G—C—G—T—T—C—A—C—C—G—G—
G—C—T—A—T—G—C—T—C—A—A—C—G—A—G—T—A—G—G—C—C—G—T—T—T—C—G—A—A—T—C—G—G—
C—G—A—A—T—G—C—G—G—A—A—C—G—T—T—G—C—T—G—C—T—C—G—A—T—G—A—A—A—T—C—G—G—
C—G—A—G—A—T—T—C—C—C—C—G—G—C—G—T—T—C—C—A—A—A—G—C—A—A—A—A—C—T—G—C—T—A—
C—C—G—T—A—A—T—A—C—A—G—G—A—A—G—G—T—T—G—A—G—C—G—A—G—T—C—G—
G—C—G—G—C—A—C—A—A—A—C—G—C—T—G—A—A—A—A—G—T—C—G—A—C—G—T—C—C—G—G—C—T—
C—A—T—A—T—T—C—G—C—C—A—C—A—A—A—T—A—A—G—G—A—T—C—T—C—G—A—A—A—T—G—G—C—G—
G—T—C—C—A—G—A—A—T—G—G—G—G—A—G—T—T—C—A—G—G—A—A—A—G—A—C—C—T—T—T—A—C—T—
A—C—C—G—C—A—T—C—A—G—C—G—G—G—G—T—G—C—C—C—T—C—A—A—T—T—T—G—C—C—G—C—C—
C—C—T—T—A—G—G—C—A—C—C—G—C—G—A—C—G—G—T—G—A—C—A—T—T—C—C—G—C—T—C—C—T—T—
G—C—A—A—G—A—G—C—A—T—T—C—C—T—T—C—A—G—C—G—G—T—T—C—A—A—C—G—A—A—G—A—G—A—
A—C—G—T—C—G—T—G—A—T—C—T—C—C—A—T—T—T—C—G—C—G—C—C—G—T—C—T—G—C—G—G—C—T—
T—G—A—C—C—A—C—T—G—T—C—G—A—A—A—G—T—T—C—C—C—T—G—G—A—A—A—A—C—
G—T—T—C—G—C—G—A—G—C—T—G—G—A—A—A—A—C—T—G—T—G—C—G—A—G—G—A—C—T—G—
C—A—A—C—T—C—T—G—C—C—A—G—G—T—C—A—A—A—G—A—C—G—A—T—C—A—C—T—T—C—C—T—C—
A—G—A—T—T—T—C—G—C—T—G—C—C—A—A—A—C—G—G—A—C—C—A—G—T—G—T—T—T—T—T—C—T—
T—C—T—C—G—C—C—T—C—T—G—G—A—A—A—G—C—G—T—C—A—C—T—G—T—T—C—G—C—A—T—G—
G—C—C—A—C—A—T—T—G—A—G—A—T—C—A—T—G—C—C—C—C—C—G—G—G—T—A—C—A—A—C—
A—C—C—G—T—T—G—C—T—C—G—G—A—C—G—C—C—A—G—C—C—A—A—T—G—A—C—G—T—T—C—C—G—
C—C—G—A—A—A—G—A—G—C—C—C—G—G—A—T—C—C—G—C—A—G—G—A—G—T—G—G—C—A—T—C—C—A—
A—T—C—T—G—A—T—C—G—A—A—G—C—G—C—C—T—G—A—A—T—T—C—C—C—T—G—A—A—A—A—C—
G—G—A—G—G—A—G—G—C—C—G—T—T—G—G—A—A—T—C—A—G—G—C—A—A—A—G—G—C—A—G—C—T—
C—G—C—A—T—C—C—T—C—G—A—A—A—A—A—A—C—G—C—C—C—C—G—G—C—A—G—T—C—G—G—G—C—
T—A—T—G—C—T—C—T—A—C—G—T—C—G—G—C—A—T—G—G—T—G—T—G—G—A—C—G—T—G—A—G—A—A—
A—G—C—T—C—T—A—A—G—C—T—G—C—C—G—G—T—G—A—3' or a functionally equivalent sequence hybridizable thereto under stringent conditions.

11. A method for activating expression of nitrogen fixation genes by placing said nitrogen fixation genes under control of a constitutively expressed activating gene product comprising the steps of (a) combining a promoter of a constitutive gene in such a position as to control a fixD gene of a Rhizobium species, wherein said activating gene codes for a product normally capable of activating R. meliloti nifHDK and fixABC promoters, thereby producing a constitutive expression of the activating gene product, (b) transforming a strain of Escherichia coli with a constitutive gene transfer system comprising a suicide vector and a transposon wherein the constitutively expressed activating gene is inserted within the transposon, (c) transferring said constitutive gene transfer system to a strain of gram-negative bacteria having said nitrogen fixation genes, and (d) selecting a recombinant strain of said gram-negative bacteria wherein said constitutively expressed activating gene is contained, replicated, and expressed in said gram-negative bacteria, thereby activating fixation of dinitrogen by activating expression of said nitrogen fixation genes.

12. A method for activating expression of nitrogen fixation genes as recited in claim 11 wherein said constitutive gene is a kanamycin resistance gene.

13. A method for activating expression of nitrogen fixation genes as recited in claim 11 wherein said constitutive gene transfer system is pSUP1011-Tn5-neopro-fixD.

14. A method for activating expression of nitrogen fixation genes as recited in claim 13 wherein said strain of gram-negative bacteria is a strain of a Rhizobium species.

15. A method for activating expression of nitrogen fixation genes as recited in claim 14 wherein said Rhizobium species is *Rhizobium meliloti*.

16. A bacterial strain containing and replicating therein a recombinant DNA molecule capable of functioning as a vector comprising,
 (a) a promoter of a *Rhizobium meliloti* fixD gene, and
 (b) a foreign structural gene under control of said promoter.

17. A bacterial strain as recited in claim 16 wherein said vector functions are derived from pSUP204.

18. A bacterial strain as recited in claim 16 wherein said promoter comprises the nucleotide sequence

```
5'-A—A—G—C—T—T—A—A—A—C—C—T—G—C—C—T—C—G—C—G—C—T—C—A—C—G—C—G—A—G—
T—C—T—T—G—C—C—C—G—G—C—C—A—A—A—T—G—C—T—A—C—G—A—G—T—T—G—A—A—T—G—A—A—A—
C—T—G—G—G—C—A—A—G—T—G—G—A—A—G—T—C—A—C—T—G—C—C—G—A—T—G—G—C—T—G—C—A—T—
G—G—A—G—T—G—C—G—G—C—A—C—A—T—G—C—A—G—A—G—T—G—T—T—G—T—G—C—G—A—G—G—C—A—
A—A—C—G—G—T—G—A—C—G—T—C—G—A—G—C—T—A—T—C—C—A—C—G—A—G—G—T—G—
G—C—T—T—C—G—T—G—T—C—C—T—C—T—T—C—A—A—G—T—T—C—G—G—A—T—G—A—G—C—C—A—C—
T—C—T—A—A—G—G—T—C—G—A—T—T—C—A—C—A—A—G—C—T—A—G—A—T—C—G—G—C—G—T—T—C—A—
A—T—A—G—G—G—G—A—C—G—A—A—G—T—G—C—C—A—G—G—G—A—T—C—C—T—T—A—C—A—A—G—A—
A—C—C—A—A—C—T—T—A—C—C—T—T—C—C—G—T—A—A—A—C—T—T—T—A—T—C—G—C—T—C—T—C—C—G—
A—C—T—G—T—C—A—A—T—A—C—G—C—A—T—A—C—C—T—C—T—A—A—T—A—T—T—A—A—G—G—G—
G—C—G—A—G—A—A—A—A—T—G—A—C—T—A—A—G—T—G—C—T—C—C—C—A—T—C—G—C—A—A—C—T—
C—G—T—T—C—A—G—G—G—G—A—G—T—T—A—G—T—G—C—C—C—T—G—T—C—T—G—T—A—C—C—T—T—C—
A—C—A—A—A—G—A—G—A—C—A—T—G—C—G—C—A—A—A—C—A—G—G—A—C—A—A—G—C—G—C—T—C—C—
G—C—C—G—A—A—A—T—T—T—A—C—A—G—C—A—T—A—T—C—A—A—A—G—G—C—T—C—T—G—3'
``` or a functionally equivalent sequence hybridizable thereto under stringent conditions.

19. A bacterial strain as recited in claim 16 wherein said foreign structural gene is a bacterial toxin gene of *Bacillus thuringiensis*.

20. A bacterial strain containing and replicating therein a recombinant DNA molecule capable of functioning as a vector comprising,
 (a) a promoter of a constitutively expressed gene, and
 (b) a coding sequence of a fixD gene of a Rhizobium species which codes for a product capable of activating *R. meliloti* nifHDK and fixABC promoters, under control of said promoter.

21. A bacterial strain as recited in claim 20 wherein said vector functions are derived from a suicide vector.

22. A bacterial strain as recited in claim 21 wherein said suicide vector comprises pSUP1011 and said vector comprises a transposon Tn5.

23. A bacterial strain as recited in claim 20 wherein said promoter is a promoter of a kanamycin resistance gene.

24. A bacterial strain as recited in claim 20 wherein said promoter of said kanamycin resistance gene comprises the nucleotide sequence

```
5'-A—C—A—G—C—A—A—G—C—G—A—A—C—C—G—G—A—A—T—T—G—C—C—A—G—C—T—G—G—G—G—C—G—
C—C—C—T—C—T—G—G—T—A—A—G—G—T—T—G—G—G—A—A—G—C—C—C—T—G—C—A—A—A—G—T—A—A—
A—C—T—G—G—A—T—G—G—C—T—T—T—C—T—T—G—C—C—G—C—C—A—A—G—G—A—T—C—T—G—A—T—G—
G—C—G—C—A—G—G—G—G—A—T—C—A—A—3'
``` or a functionally equivalent sequence hybridizable thereto under stringent conditions.

25. A bacterial strain as recited in claim 20 wherein said fixD gene comprises the nucleotide sequence

```
5'-A—T—G—G—C—C—C—C—A—C—T—C—G—T—C—T—T—G—A—G—A—C—C—A—C—G—C—T—T—A—A—C—A—
A—T—T—T—C—G—T—G—A—A—T—A—C—C—C—T—C—T—G—T—T—G—A—T—T—C—T—G—C—C—A—T—
G—C—G—C—C—G—C—G—G—C—G—G—C—A—C—T—C—G—A—G—A—T—T—C—C—G—G—C—G—T—C—G—G—A—A—
G—G—A—G—A—G—A—C—A—A—A—G—A—T—A—A—C—A—G—C—G—G—C—T—A—C—C—C—G—C—A—A—C—A—
G—C—G—G—G—T—C—T—T—C—C—T—T—C—T—G—C—C—G—C—T—G—A—T—T—A—T—A—C—T—G—T—A—C—C—A—
A—A—G—G—C—C—G—C—C—A—A—T—A—G—A—C—A—A—G—T—C—A—T—G—C—A—T—C—G—G—G—C—
G—G—C—T—G—G—T—C—G—T—A—C—C—A—G—A—C—G—T—T—G—C—A—A—C—T—C—T—G—A—G—C—T—
G—T—T—C—A—A—G—G—A—T—C—A—G—A—T—A—A—A—A—T—G—G—C—G—C—G—G—A—A—T—T—G—G—T—
C—C—G—A—C—T—G—C—C—T—T—C—A—T—C—G—C—T—G—C—G—G—C—G—G—T—G—G—A—G—G—T—C—G—
A—T—C—A—C—G—A—A—A—C—G—G—C—G—G—A—A—T—G—C—T—C—G—A—A—T—G—
C—G—C—C—G—A—A—A—G—T—C—C—G—A—T—T—A—T—G—A—T—T—A—T—G—A—G—A—G—A—G—
G—T—A—C—A—C—T—T—T—C—T—T—T—C—T—A—T—G—G—C—C—C—G—C—C—A—A—T—C—T—T—G—C—G—G—
G—G—A—G—G—G—C—C—A—T—T—C—G—G—C—T—T—C—A—T—C—G—C—A—C—A—A—T—C—A—G—C—A—G—
G—C—G—T—C—A—G—C—G—G—C—A—C—A—T—T—T—C—G—C—C—A—A—A—G—A—G—C—A—A—A—G—A—A—
C—A—A—C—A—G—A—A—T—T—C—A—C—C—G—T—G—A—T—G—A—C—A—G—A—C—C—A—G—A—G—T—T—
C—C—G—C—C—C—C—G—C—C—A—G—C—G—G—C—T—G—C—T—C—A—A—G—A—A—T—G—A—C—G—G—G—A—T—
C—A—T—C—G—G—G—G—A—A—A—G—T—A—C—C—G—C—C—C—T—C—A—T—G—A—C—G—G—C—G—G—T—A—
G—A—T—A—C—C—C—C—A—A—A—G—T—C—A—G—C—C—A—G—A—G—A—C—C—A—A—T—T—C—A—A—
T—C—G—T—T—C—T—C—C—T—T—A—G—G—G—A—G—A—A—A—C—A—G—G—A—A—C—T—G—G—C—A—A—
G—G—A—A—T—G—C—T—T—T—C—C—G—A—A—G—C—T—A—A—T—C—C—A—C—C—A—G—C—A—T—T—C—G—
A—C—T—C—G—G—C—A—A—A—A—A—A—A—G—C—C—C—T—T—C—A—T—C—A—A—G—T—C—A—A—T—T—
G—C—C—C—C—G—C—G—C—T—G—T—C—T—G—A—G—A—A—G—C—C—T—T—C—T—C—G—A—A—T—C—A—G—A—
G—C—T—G—T—T—G—G—A—C—A—T—G—A—A—A—G—G—T—G—C—G—T—T—C—A—C—C—G—G—
G—C—T—A—T—T—G—C—T—C—A—A—C—G—A—G—T—A—G—G—C—C—G—T—T—C—G—A—A—T—C—G—G—
C—G—A—A—T—G—C—G—G—A—A—C—G—T—T—G—C—T—G—C—T—C—G—A—T—G—A—A—A—T—C—G—G—
C—G—A—G—A—T—T—C—C—C—C—C—G—G—C—G—T—C—C—A—A—C—A—A—A—A—C—C—T—G—C—T—A—
C—G—C—G—T—A—A—T—A—C—C—G—G—G—A—A—G—G—G—A—A—T—T—T—G—G—C—G—A—G—T—C—G—
G—C—G—G—C—A—C—A—A—A—G—A—C—G—C—T—G—A—A—A—G—T—C—G—A—C—G—T—C—C—G—G—C—T—
C—A—T—A—T—T—C—G—C—C—A—C—A—A—A—T—A—A—G—G—A—T—C—T—C—G—A—A—A—T—G—G—C—G—
G—T—C—C—A—G—A—A—T—G—G—G—G—A—G—T—T—C—A—G—G—G—A—A—G—A—C—C—T—T—T—A—C—T—
```

```
A—C—G—C—A—T—C—A—G—C—G—G—G—T—G—C—C—C—T—C—A—T—T—T—G—C—C—G—C—C—
C—C—T—T—A—G—C—A—C—C—G—C—G—A—C—G—G—T—G—A—C—A—T—T—C—C—G—C—T—C—C—T—T—
G—C—A—A—G—A—G—C—A—T—T—C—C—T—T—C—A—G—C—G—G—T—T—C—A—A—C—G—A—A—G—A—G—A—
A—C—G—T—C—G—T—G—A—T—C—T—C—C—A—T—T—T—C—G—C—G—C—C—G—T—C—T—G—C—G—C—T—
T—G—A—C—C—A—C—T—T—G—T—C—G—A—A—G—T—G—C—A—A—G—T—T—C—C—C—T—G—A—A—A—C—
G—T—T—C—G—C—G—A—G—C—T—G—G—A—A—A—A—C—T—G—T—G—T—G—C—G—G—A—G—G—A—C—T—G—
C—A—A—C—T—C—T—C—G—C—C—A—G—G—T—C—A—A—A—G—A—C—G—A—T—C—A—C—T—T—C—C—T—C—
A—G—A—T—T—T—C—G—C—C—T—G—C—C—A—A—A—A—C—G—G—A—C—C—A—G—T—G—T—T—T—T—C—T—
T—C—T—T—C—G—C—C—T—C—T—G—G—A—A—A—A—G—G—C—G—T—T—C—A—C—T—G—T—T—C—G—C—A—T—G—
G—C—C—A—C—A—T—T—G—A—G—A—T—C—C—A—T—G—C—G—C—C—G—C—G—G—T—A—C—A—A—C—
A—C—C—G—T—T—G—C—T—C—G—G—A—G—C—G—C—C—A—G—C—C—A—A—T—G—A—C—G—T—T—C—C—G—
C—C—G—A—A—A—G—A—G—C—C—C—G—G—A—T—C—C—G—C—A—G—G—A—G—T—G—G—C—A—T—C—C—A—
A—T—C—T—G—A—T—C—G—A—G—C—C—G—A—C—C—C—T—T—G—A—T—C—A—G—T—G—C—C—G—C—T—
G—G—A—G—G—A—G—G—C—C—C—G—T—T—G—G—A—A—T—C—A—G—G—C—A—A—A—G—G—C—A—G—C—T—
C—G—C—A—T—C—C—T—C—G—A—A—A—A—A—A—C—G—C—C—C—C—G—G—C—A—G—G—T—C—G—G—G—C—
T—A—T—G—C—T—C—T—A—C—G—T—C—G—G—C—A—T—G—T—G—T—T—G—G—A—C—G—T—G—A—G—A—A—
A—G—C—T—C—T—A—A—G—C—T—G—C—C—G—G—T—G—A—3'
``` or a functionally equivalent sequence hybridizable thereto under stringent conditions.

* * * * *